United States Patent
Kodoma et al.

(10) Patent No.: US 6,432,957 B1
(45) Date of Patent: Aug. 13, 2002

(54) PIPERAZINE DERIVATIVE

(75) Inventors: Tatsuhiko Kodoma, Tokyo; Masahiro Tamura, Higashimurayama; Toshiaki Oda, Higashimurayama; Yukiyoshi Yamazaki, Higashimurayama; Masahiro Nishikawa, Higashimurayama; Takeshi Doi, Higashimurayama; Yoshinori Kyotani, Higashiyamato, all of (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

(21) Appl. No.: 09/893,681

(22) Filed: Jun. 29, 2001

(51) Int. Cl.[7] .................... A61K 31/496; C07D 401/06
(52) U.S. Cl. ................... 514/252.13; 544/360
(58) Field of Search ................ 514/255.05, 252.13; 544/360, 358

(56) References Cited

U.S. PATENT DOCUMENTS

| | | | |
|---|---|---|---|
| 4,029,650 A | * | 6/1977 | Raynaud et al. |
| 4,565,816 A | * | 1/1986 | Neumann |
| 4,876,256 A | * | 10/1989 | Coss et al. |
| 5,135,931 A | * | 8/1992 | Carlier et al. |
| 5,780,472 A | * | 7/1998 | Cho et al. |
| 5,965,560 A | * | 10/1999 | Glase et al. |
| 6,258,813 B1 | * | 7/2001 | Arlt et al. ............ 514/252.11 |

FOREIGN PATENT DOCUMENTS

| | | |
|---|---|---|
| JP | 9-143075 | 6/1997 |
| JP | 10-67656 | 3/1998 |
| JP | 10-147568 | 6/1998 |
| JP | 10-182550 | 7/1998 |
| JP | 11-92382 | 4/1999 |
| JP | 2000-86641 | 3/2000 |
| JP | 2000-509070 | 7/2000 |
| JP | 2000-319277 | 11/2000 |

OTHER PUBLICATIONS

CA:130:37228 abs of Clin. Exp. Immunol. by Moore et al 114(1) pp 73–77 1998.*
CA:125:244411 abs of Br. J. Cancer by Griffiths et al. 74(4) pp. 579–584 1996.*
CA:135:105998 abs of J Am Chem. Soc. Nephrol. by Patrakka et al 12(2) pp 289–296 2001.*
CA: 67:100103 abs of J Med. Chem. 10 (5) pp 812–18 by Jain et al. 1967.*
CA:68:59531 abs of akad. Med. Warsaw by Biniecki et al 24(3) pp 225–9 1967.*

09/893,682 Tatsuhiko Kodama et al.
Y. Ohkawara et al., "In SITU Expression of the Cell Adhesion Molecules in Bronchial Tissues Form Asthmatics with Air Flow Limitation: In Vivo Evidence of VCAM–1/VLA–4 Interaction in Selective Eosinophil Infiltration", *American Journal of Respiratory Cell and Molecular Biology*, 1995, vol. 12, pp. 4–12.
A. Sakai, et al., "P–Selection and Vascular Cell Adhesion Molecule–1 Are Focally Expressed in Aortas of Hypercholesterolemic Rabbits Before Intimal Accumulations of macrophages and T Lymphocytes", *Arteriosclerosis, Thrombosis, and Vascular Biology*, Feb. 1997, vol. 17, No. 2, pp. 310–316.
H. Wakita, et al., "E–Selectin and vascular cell adhesion molecule–1 as critical adhesion molecules for infiltration of T. Lymphocytes and Eosinophils in atopic dermatitis", *Journal of Cutaneous Pathology*, 1994, pp. 33–39.
T. Satoh et al., "Cyclophosphamide–induced blood and tissue eosinophilia in contact sensitivity mechanism of hapten–induced eosinophil recruitment into the skin", *European Journal of Immunology*, 1997, vol. 27, pp. 85–91.

* cited by examiner

*Primary Examiner*—Jean F. Vollano
(74) *Attorney, Agent, or Firm*—Oblon, Spivak, McClelland, Maier & Neustadt, P.C.

(57) ABSTRACT

A piperazine compound represented by formula (1):

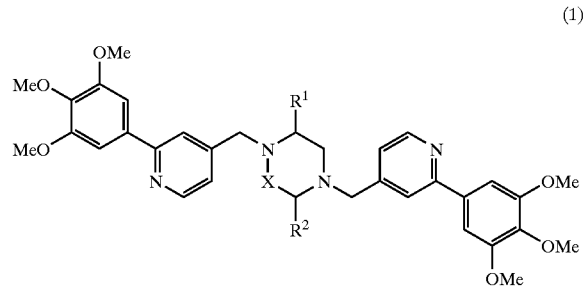

(1)

wherein X is —$CH_2$—, —C(O)— or —$CH(CH_3)$—; $R^1$ is a hydrogen atom or alkyl group; and $R^2$ is a hydrogen atom, alkyl group, hydroxyalkyl group, arylalkyl group, heteroarylalkyl group, carboxyalkyl group, carboxamidoalkyl group, aminoalkyl group or guanidinoalkyl group; an acid-addition salt thereof, or a hydrate thereof. The compound has excellent inhibitory effects on both cell adhesion and cell infiltration and is useful for prevention or treatment of diseases such as allergy, asthma, rheumatism, arteriosclerosis and inflammation.

21 Claims, No Drawings

PIPERAZINE DERIVATIVE

BACKGROUND OF THE INVENTION

1. Field of the Invention

The present invention relates to novel cyclic diamine compounds which have inhibitory effects on both cell adhesion and cell infiltration and are useful as anti-asthmatic agents, anti-allergic agents, anti-rheumatic agents, anti-arteriosclerotic agents, anti-inflammatory agents or the like, and medicines containing such compounds.

2. Description of the Background Art

In various inflammatory diseases, infiltration of leukocytes into inflammatory sites is observed. For example, infiltration of eosinophils into the bronchus in asthma (Ohkawara, Y. et al., Am. J. Respir. Cell Mol. Biol., 12, 4–12 (1995)), infiltration of macrophages and T lymphocytes into the aorta in arteriosclerosis (Sakai, A. et al., Arterioscler Thromb. Vasc. Biol., 17, 310–316 (1997)), infiltration of T lymphocytes and eosinophils into the skin in atopic dermatitis (Wakita H. et al., J. Cutan. Pathol., 21, 33–39 (1994)) or contact dermatitis (Satoh, T. et al., Eur. J. Immunol., 27, 85–91 (1997)), and infiltration of various leukocytes into rheumatoid synovial tissue (Tak, P P. et al., Clin. Immunol. Immunopathol., 77, 236–242 (1995)), have been reported.

Infiltration of these leukocytes is elicited by cytokines, chemokines, lipids, and complements produced in inflammatory sites (Albelda, S M. et al., FASEB J., 8, 504–512 (1994)). Activated leukocytes adhere to vascular endothelial cells through an interaction called rolling or tethering with endothelial cells activated likewise. Thereafter, the leukocytes transmigrate through endothelium to infiltrate into the inflammatory sites (Springer, T A., Annu. Rev. Physiol., 57, 827–872 (1995)). In the adhesion of leukocytes to the vascular endothelial cells in this process, various cell adhesion molecules such as an immunoglobulin superfamily (ICAM-1, VCAM-1 and the like), a selectin family (E-selectin and the like), an integrin family (LFA-1, VLA-4 and the like) and CD44, which are induced on the surfaces of the cells by stimulation by cytokines or the like, play important roles ("Rinsho Meneki (Clinical Immune)", 30, Supple. 18 (1998)), and a relationship between the disorder state and aberrant expression of the cell adhesion molecules is noted.

Accordingly, an agent capable of inhibiting cell adhesion can be useful as an agent for preventing and treating allergic diseases such as bronchial asthma, dermatitis, rhinitis and conjunctivitis; autoimmune diseases such as rheumatoid arthritis, nephritis, inflammatory bowel diseases, diabetes and arteriosclerosis; and chronic inflammatory diseases. In fact, it has been reported that antibodies against adhesion molecules on leukocytes such as LFA-1, Mac-1 and VLA-4 or antibodies against ICAM-1, VCAM-1, P-selectin, E-selectin and the like on vascular endothelial cells, which become ligands thereof, inhibit infiltration of leukocytes into inflammatory sites in animal models. For example, neutralizing antibodies against VCAM-1 and VLA-4, which is a counter receptor thereof, can delay development of diabetes in an NOD mouse model which spontaneously causes the diabetes (Michie, S A. et al., Curr. Top. Microbiol. Immunol., 231, 65–83 (1998)). It has also been reported that an antibody against VLA-4 or ICAM-1 and its counter receptor, LFA-1, inhibits infiltration of eosinophils in a guinea pig and mouse allergic conjunctivitis model (Ebihara et al., Current Eye Res., 19, 20–25 (1999); Whitcup, S M et al., Clin. Immunol., 93, 107–113 (1999)), and a monoclonal antibody against VCAM-1 inhibits infiltration of leukocytes in mouse DSS-induced colitis model to attenuate colitis (Soriano, A. et al., Lab. Invest., 80, 1541–1551 (2000)). Further, an anti-VLA-4 antibody and an anti-CD44 antibody reduce the incidence of disease symptoms in a mouse collagen arthritis model (Zeidler, A. et al., Autoimmunity, 21, 245–252 (1995)). Even in cell adhesion molecule deficient-mice, inhibition of infiltration of leukocytes into inflammatory tissues is observed likewise in inflammatory models (Bendjelloul, F. et al., Clin. Exp. Immunol., 119, 57–63 (2000); Wolyniec, W W. et al., Am. J. Respir. Cell Mol. Biol., 18, 777–785 (1998); Bullard, DC. et al., J. Immunol., 157, 3153–3158 (1996)).

However, it is difficult to develop antibody-based drugs because they are polypeptides and so oral administration is a problem. Moreover, problems of the possible side effects due to antigenicity and allergic reactions are problems.

On the other hand, there have been various investigations of low-molecular weight compounds having an inhibitory effect on cell adhesion with a view toward permitting oral administration. These compounds include benzothiophene derivatives (Boschelli, D H. et al., J. Med. Chem., 38, 4597–4614 (1995)), naphthalene derivatives (Japanese Patent Application Laid-Open No. 10-147568), hydroxybenzoic acid derivatives (Japanese Patent Application Laid-Open No. 10-182550), lignans (Japanese Patent Application Laid-Open No. 2000-086641 through PCT route), condensed pyrazine compounds (Japanese Patent Application Laid-Open No. 2000-319277 through PCT route), 2,6-dialkyl-4-silylphenol (Japanese Patent Application Laid-Open Re-Publication No. 2000-509070 through PCT route) and the like. However, the goal has not often been sufficiently achieved under the circumstances. Cyclic diamine compounds described in Japanese Patent Application Laid-Open Nos. 9-143075 and 11-92382 do not exhibit a sufficient inhibitory effect on cell adhesion, and there is a demand for further improvement in activity.

SUMMARY OF THE INVENTION

An object of the present invention is to provide a substance having inhibitory effects on both cell adhesion and cell infiltration, plus excellent anti-asthmatic effects, anti-allergic effects, anti-rheumatic effects, anti-arteriosclerotic effects and anti-inflammatory effects.

With the foregoing circumstances in mind, the present inventors carried out an extensive investigation to find a substance which inhibits cell adhesion and cell infiltration. As a result, we found that compounds represented by the general formula (1) have excellent cell adhesion-inhibiting effects and cell infiltration-inhibiting effects and are useful as anti-allergic agents, anti-asthmatic agents, anti-rheumatic agents, anti-arteriosclerotic agents or anti-inflammatory agents.

The present invention provides a piperazine compound represented by the following general formula (1):

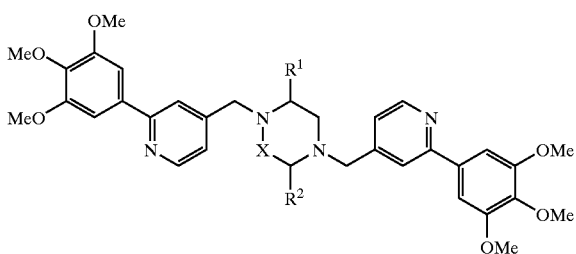

wherein X is —CH$_2$—, —C(O)— or —CH(CH$_3$)—; R$^1$ is a hydrogen atom or alkyl group; and R$^2$ is a hydrogen atom, alkyl group, hydroxyalkyl group, arylalkyl group, heteroarylalkyl group, carboxyalkyl group, carboxamidoalkyl group, aminoalkyl group or guanidinoalkyl group;

an acid-addition salt thereof, or a hydrate thereof.

According to the present invention, there is also provided a medicine comprising the above piperazine compound, the acid-addition salt thereof, or the hydrate thereof as an active ingredient.

According to the present invention, there is further provided a medicinal composition comprising the above piperazine compound, the acid-addition salt thereof, or the hydrate thereof and a pharmaceutically acceptable carrier.

According to the present invention, there is still further provided a method for treating a disease caused by cell adhesion and/or cell infiltration, which comprises administering an effective amount of the above piperazine compound, the acid-addition salt thereof, or the hydrate thereof to a patient who requires the treatment.

DETAILED DESCRIPTION OF THE PREFERRED EMBODIMENTS

The alkyl groups represented by R$^1$ and R$^2$ are preferably C$_1$–C$_6$-alkyl groups, and specific examples include methyl, ethyl, n-propyl, isopropyl, n-butyl, isobutyl, sec-butyl, tert-butyl, pentyl and hexyl groups, with methyl, ethyl, n-propyl, isopropyl, isobutyl and sec-butyl groups being particularly preferred.

The hydroxyalkyl group represented by R$^2$ is a hydroxy-C$_1$–C$_6$-alkyl group, and specific examples thereof include hydroxymethyl, 2-hydroxyethyl, 2-hydroxy-1-methylethyl, 2-hydroxy-1,1-dimethylethyl, 3-hydroxypropyl, 3-hydroxy-2-methylpropyl, 4-hydroxybutyl, 5-hydroxypentyl and 6-hydroxyhexyl groups, with hydroxymethyl, 2-hydroxyethyl, 2-hydroxy-1-methylethyl, 2-hydroxy-1,1-dimethylethyl and 3-hydroxypropyl groups being particularly preferred. The arylalkyl group is preferably a C$_6$–C$_{10}$-aryl-C$_1$–C$_6$-alkyl groups, and specific examples thereof include phenyl-C$_1$–C$_6$-alkyl groups such as benzyl and phenethyl groups. The heteroarylalkyl group is preferably a 5- or 6-membered heteroaryl-C$_1$–C$_6$-alkyl group having 1 or 2 nitrogen atoms, and preferable examples thereof include pyridyl-C$_1$–C$_6$-alkyl groups, pyrimidyl-C$_1$–C$_6$-alkyl groups, imidazolyl-C$_1$–C$_6$-alkyl groups and pyrrolyl-C$_1$–C$_6$-alkyl groups. The carboxyalkyl group is preferably a carboxy-C$_1$–C$_6$-alkyl group, and specific examples thereof include carboxymethyl and carboxyethyl groups. The carboxamidoalkyl group is a carboxamido-C$_1$–C$_6$-alkyl group, and specific examples thereof include carboxamidomethyl and carboxamidoethyl. The aminoalkyl group is preferably a amino-C$_1$–C$_6$-alkyl group, and specific examples thereof include aminomethyl, aminoethyl and aminopropyl groups.

The guanidinoalkyl group is preferably a guanidino-C$_1$–C$_6$-alkyl group, and specific examples thereof include guanidinomethyl, guanidinoethyl and guanidinopropyl groups.

No particular limitation is imposed on the acid-addition salts of the compounds (1) according to the invention as long as they are pharmaceutically acceptable salts. Examples include the acid-addition salts of mineral acids, such as hydrochlorides, hydrobromides, hydriodides, sulfates and phosphates; and acid-addition salts of organic acids, such as benzoates, methanesulfonates, ethanesulfonates, benzenesulfonates, p-toluenesulfonates, oxalates, maleates, fumarates, tartrates, citrates and acetates.

The compounds of formula (1) may be present in the form of solvates typified by hydrates, and the solvates are embraced in the present invention. Optical isomers are present in the compounds (1) according to the present invention, and all the isomers are also embraced in the present invention.

Among the compounds (1) those in which X is —CH(CH$_3$)— or —CH$_2$— can be prepared in accordance with, for example, a process shown in the following reaction formula:

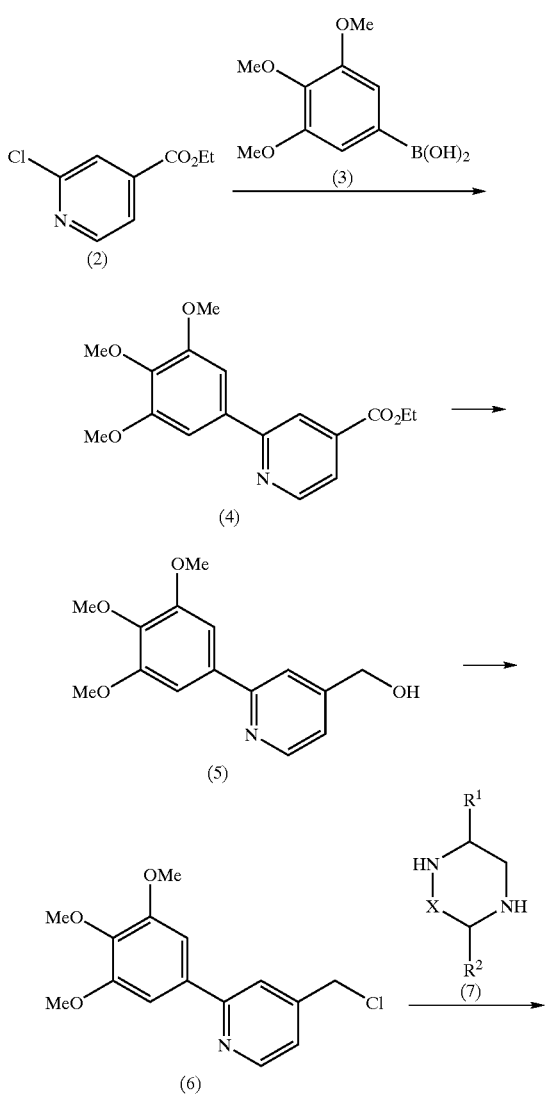

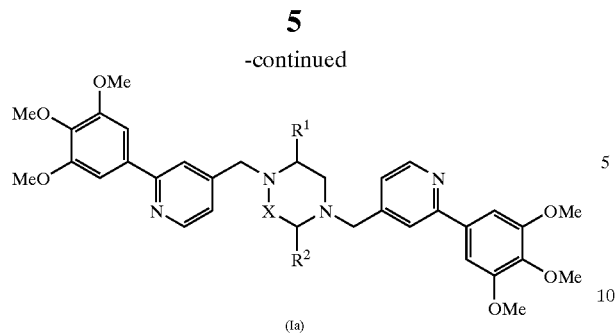

(Ia)

wherein X is —CH(CH₃)— or —CH₂—, and $R^1$ and $R^2$ have the same meanings as defined above.

More specifically, a chlorinated compound (2) is reacted with 3,4,5-trimethoxyphenylboronic acid (3) at 0° C. to reflux temperature, preferably 90° C. for 10 minutes to several days, preferably 5 hours in the presence of a metal catalyst such as tetrakis(triphenylphosphine)palladium(0) and a base such as 2 M sodium carbonate in a solvent such as toluene, benzene, tetrahydrofuran (THF), dioxane or acetonitrile, thereby obtaining a condensate (4). This compound is reacted with lithium aluminum hydride at −20° C. to room temperature, preferably at 0° C. for several seconds to several hours, preferably 30 minutes in THF, thereby giving an alcohol (5). The compound (5) is stirred together with thionyl chloride at −20° C. to room temperature, preferably 0° C. for 1 hour to several days, preferably 5 hours in a solvent such as chloroform, dichloromethane, ethyl acetate, ether, THF or dioxane, thereby obtaining a chloro-derivative (6). The compound (6) and a diamine (7) are stirred at room temperature to 100° C., preferably 50° C. for 1 hour to several days, preferably 5 hours in the presence of potassium carbonate in a solvent such as N,N-dimethylformamide (DMF), dimethyl sulfoxide (DMSO) or acetonitrile, thereby obtaining a compound (1a) according to the present invention.

Among compounds (1), those in which X is —C(O)— can be prepared in accordance with, for example, a process shown in the following reaction formula:

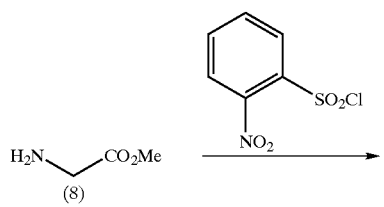

(8)

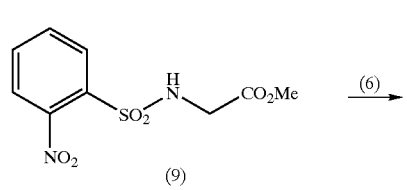

(9)

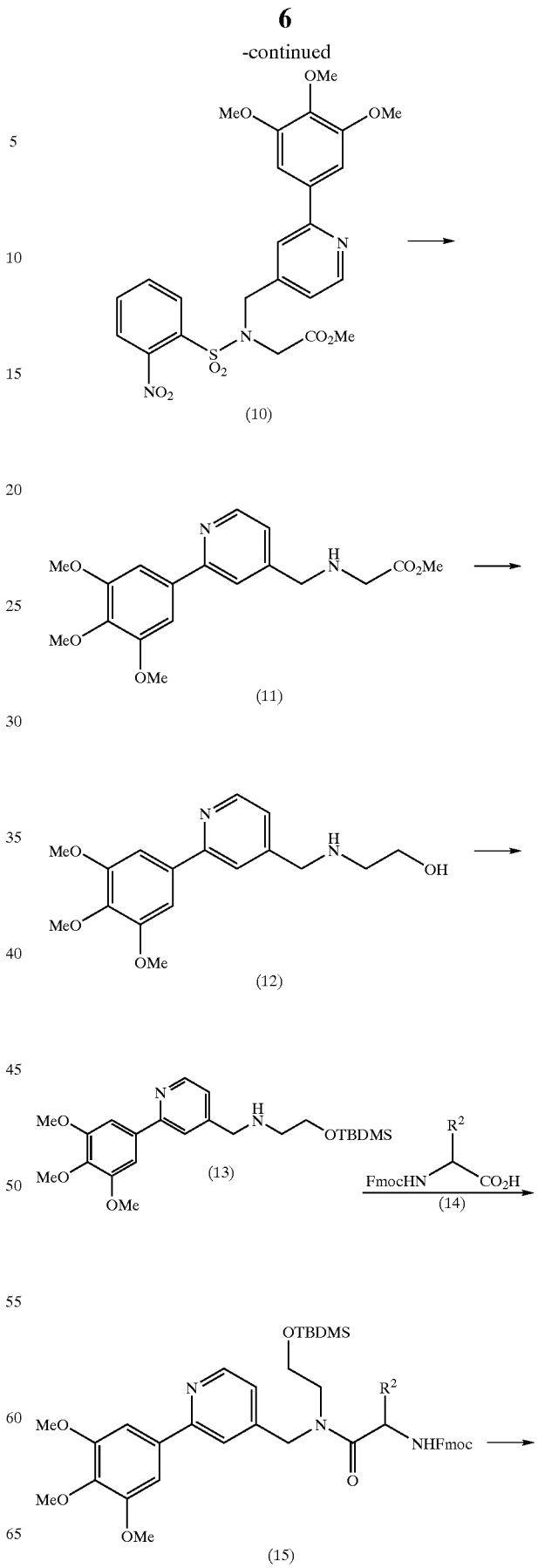

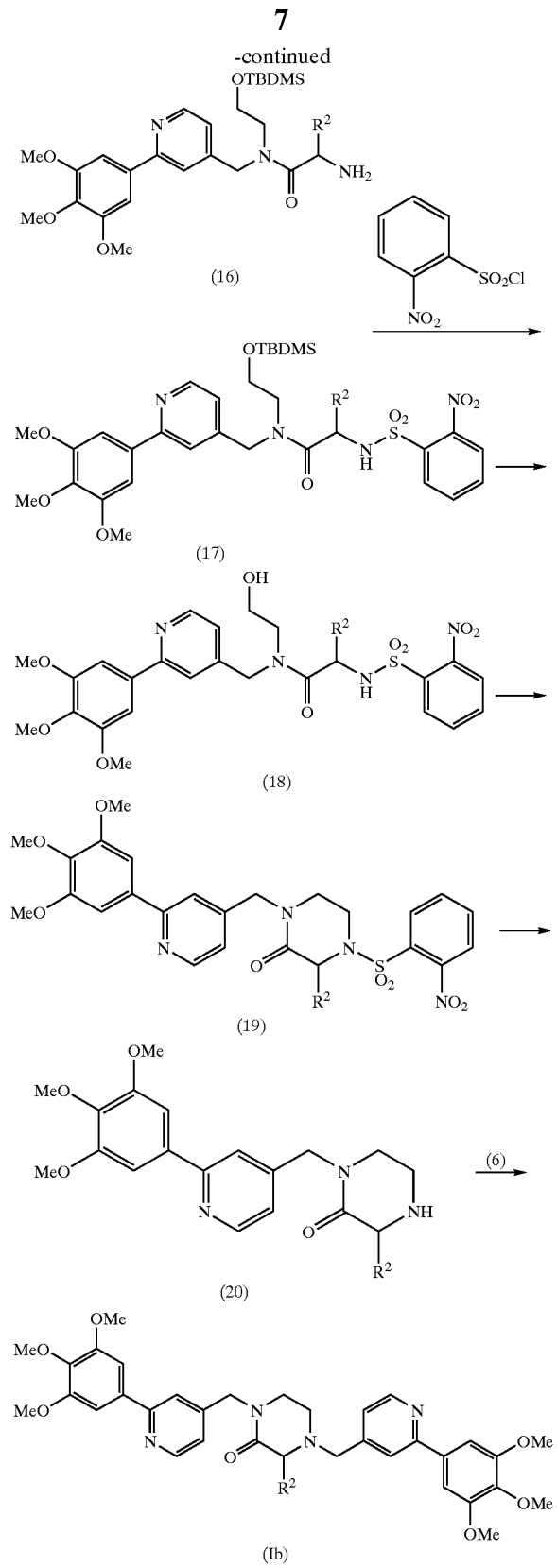

2-nitrobenzenesulofonylated compound (9). The above-described chloro-derivative (6) is reacted with the compound (9) under the same conditions as described above to obtain a compound (10). The compound (10) is treated by an already known method, thereby obtaining a compound (11). The compound (11) is reduced by lithium aluminum hydride under the same conditions as described above, thereby obtaining an alcohol (12). The compound (12) is reacted with tert-butyldimethylsilyl chloride (TBDMS-Cl) at 0° C. to reflux temperature, preferably 50° C. for 1 hour to several days, preferably a night in the presence of a base such as imidazole, triethylamine or 4-methylmorpholine and 4-(dimethylamino)pyridine in a solvent dichloromethane, acetonitrile or DMF to obtain a TBDMS-derivative (13). The compound (13) is reacted with 9-fluorenylmethoxycarbonyl-amino acid (Fmoc-amino acid) (14) at 0° C. to reflux temperature, preferably room temperature for 1 minute to several days, preferably 10 minutes in the presence of a dehydration-condensing agent such as dicyclohexylcarbodiimide, 1-ethyl-3-(3-dimethylaminopropyl)carbodiimide hydrochloride (water-soluble carbodiimide hydrochloride) or O-(1H-benzotriazol-1-yl)-N,N,N',N'-tetramethyluronium hexafluorophosphate (HBTU) in a solvent such as chloroform, dichloromethane, acetonitrile, THF, DMF or DMSO, thereby obtaining a compound (15). The compound (15) is reacted with piperidine in accordance with an already known method, thereby obtaining an amine derivative (16). The compound (16) is reacted with the above-described 2-nitrobenzenesulfonyl chloride under the same conditions as described above to obtain a 2-nitrobenzenesulfonylated compound (17). The compound (17) is treated by an already known method, thereby obtaining an alcohol (18). The compound (18) is dissolved in a solvent such as THF or dioxane and reacted with triphenylphosphine and diethyl azodicarboxylate (DEAD) at 0° C. to reflux temperature, preferably room temperature for 1 hour to several days, preferably a night, thereby obtaining a compound (19). The compound (19) is subjected to de-2-nitrobenzenesulfonylation by an already known method to obtain a compound (20). The above-described chloro-derivative (6) is reacted with the compound (20) under the same conditions as described above, thereby obtaining a compound (1b) according to the present invention.

Among the compounds (1) according to the present invention, those in which X is —CH$_2$— can be prepared in accordance with, for example, a process shown in the following reaction formula:

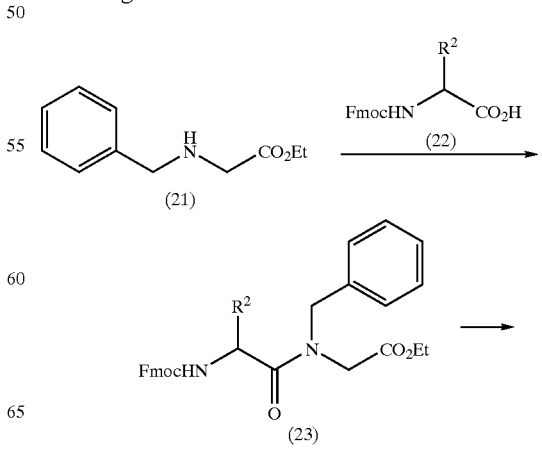

wherein X is —C(O)—, and R$^1$ and R$^2$ have the same meanings as defined above.

More specifically, a glycine methyl ester (8) is reacted with 2-nitrobenznesulfonyl chloride in accordance with an already known method, thereby obtaining a

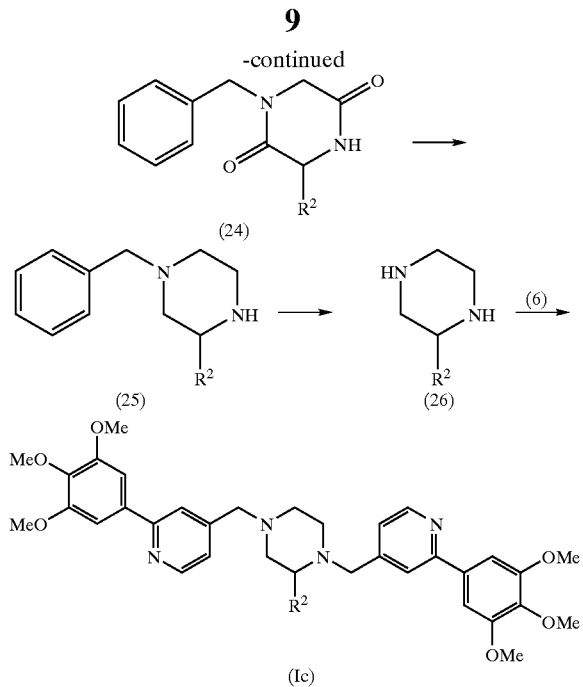

wherein X is —CH$_2$—, and R$^1$ and R$^2$ have the same meanings as defined above.

More specifically, an N-benzylglycine methyl ester (21) is reacted with Fmoc-amino acid (22) in accordance with an already known method, thereby obtaining a dipeptide derivative (23). The compound (23) is subjected to de-Fmoc and cyclization at the same time in accordance with an already known method to obtain a diketopiperazine derivative (24). The compound (24) is treated by an already known reduction method making use of lithium aluminum hydride or the like, thereby obtaining a piperazine derivative (25). The compound (25) is subjected to de-benzylation by already known catalytic reduction making use of palladium on carbon, thereby obtaining a compound (26). The compound (26) is reacted with the above-described chloro-derivative (6) under the same conditions as described above, thereby obtaining a compound (1c) according to the present invention.

The compounds (1) according to the present invention are obtained by any of the above-described processes and may further be purified by using an ordinary purification means such as recrystallization or column chromatography as needed. As needed, the compounds may also be converted into the desired salts or solvates in a method known per se in the art. When the compounds (1) include configurational isomers, the present invention include any isomers.

The compounds (1) according to the present invention, or acid-addition salts or solvates thereof thus obtained have an excellent inhibitory effect of cell adhesion as demonstrated in the Examples, which will be described subsequently, and are useful as medicines for treatment or prevention of diseases of animals including human, such as asthma, allergy, rheumatism, arteriosclerosis and inflammation.

The medicine according to the present invention comprises a compound (1), a salt thereof, or a solvate thereof as an active ingredient. The form of administration may be suitably selected as necessary for the therapeutic application intended without any particular limitation, including oral preparations, injections, suppositories, ointments, inhalants, eye drops, nose drops and plasters. A composition suitable for use in these administration forms can be prepared by blending a pharmaceutically acceptable carrier in accordance with the conventional preparation method publicly known by those skilled in the art.

When an oral solid preparation is formulated, an excipient, and optionally, a binder, a disintegrator, a lubricant, a colorant, a taste corrigent, a smell corrigent and the like are added to compound (1), and the resultant composition can be formulated into tablets, coated tablets, granules, powders, capsules, etc. in accordance with methods known in the art.

As such additives described above, any additives may be used which are generally used in the pharmaceutical field. Examples thereof include excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dry starch, sodium alginate, agar powder, sodium hydrogencarbonate, calcium carbonate, sodium lauryl sulfate, monoglyceryl stearate and lactose; lubricants such as purified talc, stearic acid salts, borax and polyethylene glycol; and taste corrigents such as sucrose, orange peel, citric acid and tartaric acid.

When an oral liquid preparation is formulated, a taste corrigent, buffer, stabilizer, smell corrigent and/or the like are added to compound (1), and the resulting composition can be formulated into internal liquid preparations, syrup preparations, elixirs, etc. in accordance with methods known in the art. In this case, vanillin as the taste corrigent, may be used. As the buffer, sodium citrate may be mentioned. As examples of the stabilizer, tragacanth, gum arabic and gelatin may be mentioned.

When an injection is formulated, a pH adjustor, buffer, stabilizer, isotonicity agent, local anesthetic and the like may be added to the compound (1) according to the present invention, and the resulting composition can be formulated into subcutaneous, intramuscular and intravenous injections in accordance with methods known in the art. Examples of the pH adjustor and buffer in this case include sodium citrate, sodium acetate and sodium phosphate. Examples of the stabilizer include sodium pyrosulfite, EDTA, thioglycolic acid and thiolactic acid. Examples of the local anesthetic include procaine hydrochloride and lidocaine hydrochloride. Examples of the isotonicity agent include sodium chloride and glucose.

When a suppository is formulated, a carrier preparation known in the art, for example, polyethylene glycol, lanoline, cacao butter, fatty acid triglyceride or the like, and optionally, a surfactant such as Tween (trade mark) and the like are added to the compound (1), and the resultant composition can be formulated into suppositories in accordance with methods known in the art.

When an ointment is formulated, a base material, stabilizer, wetting agent, preservative and the like, which are generally used, are blended with compound (1) as needed, and the resulting blend is mixed and formulated into ointments in accordance with known methods. Examples of the base material include liquid paraffin, white vaseline, bleached beeswax, octyldodecyl alcohol and paraffin. Examples of the preservative include methyl p-hydroxybenzoate, ethyl p-hydroxybenzoate and propyl p-hydroxybenzoate.

Besides the above preparations, inhalants, eye drops and nose drops may also be formulated in accordance with known methods.

The dose of the medicine according to the present invention varies according to the age, weight and condition of the patient to be treated, the administration method, the number of times of administration, and the like. It is however preferred that the medicine is generally orally or parenterally administered at once or in several portions in a dose of 1 to 1,000 mg per day in terms of compound (1), for an adult.

The present invention will hereinafter be described in more detail by Examples. However, the present invention is not limited to these examples.

PREPARATION EXAMPLE 1

Synthesis of Ethyl 2-(3,4,5-trimethoxyphenyl) isonicotinate 3,4,5-Trimethoxyphenylboronic acid (20.64 g) and ethyl 2-chloroisonicotinate (19.06 g) were suspended in a mixed solvent of toluene (200 mL) and THF (100 mL), and to the suspension 2 M sodium carbonate (200 mL) and tetrakis (triphenylphosphine)palladium(0) (5.93 g) were added. The mixture was stirred overnight at 90° C. under an argon atmosphere. Ethyl acetate was added to the reaction mixture to separate an organic layer. The organic layer was washed with saturated brine, dried over anhydrous magnesium sulfate and concentrated under reduced pressure. The residue was purified by column chromatography on silica gel (hexane:ethyl acetate=5:1) to obtain the title compound.

Yield: 27.70 g (85%).

$^1$H-NMR (400 MHz, CDCl$_3$) δ: 1.45(t,3H,J=7.0 Hz), 3.92(s,3H), 3.99(s,6H), 4.46(q,2H,J=7.0 Hz), 7.30(s,2H), 7.76(dd,1H,J=5.1 Hz,1.6 Hz), 8.24(dd,1H,J=1.6 Hz,0.8 Hz), 8.81(dd,1H,J=5.1 Hz,0.8 Hz).

PREPARATION EXAMPLE 2

Synthesis of 4-hydroxymethyl-2-(3,4,5-trimethoxyphenyl)-pyridine

Ethyl 2-(3,4,5-trimethoxyphenyl)nicotinate (27.70 g) was dissolved in THF (200 mL), and to the solution lithium aluminum hydride (3.31 g) was added at 0° C. under an argon atmosphere, and the mixture was stirred at 0° C. for 1 hour as it is. A small amount of water and then sodium sulfate were added to the reaction mixture, and the reaction mixture was filtered through celite. The filtrate was concentrated under reduced pressure, and the resultant crystals were recrystallized from ethyl acetate-hexane to obtain the title compound.

Yield: 18.15 g (76%).

$^1$H-NMR (400 MHz, CDCl$_3$) δ: 3.90(s,3H), 3.95(s,6H), 4.79(s,2H), 7.19(d,1H,J=5.1 Hz), 7.21(s,2H), 7.66(s,1H), 8.60(d,1H,J=5.1 Hz).

PREPARATION EXAMPLE 3

Synthesis of 4-chloromethyl-2-(3,4,5-trimethoxyphenyl)-pyridine:

4-Hydroxymethyl-2-(3,4,5-trimethoxyphenyl)pyridine (18.15 g) was dissolved in chloroform (300 mL), and to the solution thionyl chloride (19.2 mL) was added at 0° C.. After 30 minutes, the mixture was warmed to room temperature and stirred for 4 hours. The reaction mixture was washed with water and saturated brine, dried over anhydrous sodium sulfate and concentrated under reduced pressure. The resultant crystals were then recrystallized from chloroform-hexane to obtain the title compound.

Yield: 17.87 g (92%).

$^1$H-NMR (400 MHz, CDCl$_3$) δ: 3.91(s,3H), 3.97(s,6H), 4.61 (s,2H), 7.24(s,2H), 7.26(d,1H,J=5.1 Hz), 7.68(s,1H), 8.67(d,1H,J=5.1 Hz).

EXAMPLE 1

Synthesis of cis-N,N'-bis[[2-(3,4,5-trimethoxyphenyl)pyridin-4-yl]methyl]-2,6-dimethylpiperazine tetrahydrochloride

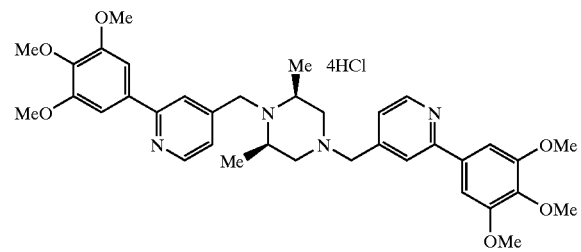

4-Chloromethyl-2-(3,4,5-trimethoxyphenyl)pyridine (123 mg) and cis-2,6-dimethylpiperazine (23 mg) were dissolved in DMF (5 mL), and to the solution potassium carbonate (58 mg) was added. The mixture was stirred at 80° C. for 4 hours and concentrated under reduced pressure. Water was added to the residue to conduct extraction with chloroform. The resultant organic layer was washed with saturated brine, dried over anhydrous magnesium sulfate and then concentrated under reduced pressure. The residue was purified by column chromatography on silica gel (chloroform:methanol=40:1) to obtain a free base of the title compound. This compound was dissolved in ethyl acetate, and to the solution an ethyl acetate solution of 4 M hydrogen chloride was added to provide a hydrochloride.

Yield: 101 mg (68%).

$^1$H-NMR (measured as a free base, 400 MHz, CDCl$_3$) δ: 0.97(d,6H,J=6.1 Hz), 1.99(t,2H,J=11.1 Hz), 2.75(d,4H,J= 9.8 Hz), 3.53(s,2H), 3.81(s,2H), 3.90(s,6H), 3.97(s,6H),3.98 (s,6H), 7.22–7.24(m,5H), 7.32(d,1H,J=4.3 Hz), 7.64(s,1H), 7.67(s,1H), 8.57(d,1H,J=5.1 Hz), 8.61(d,1H,J=5.1 Hz). m/z (EI): 628 [M$^+$].

EXAMPLE 2

Synthesis of trans-N,N'-bis[[2-(3,4,5-trimethoxyphenyl)-pyridin-4-yl]methyl]-2,5-dimethylpiperazine tetrahydrochloride

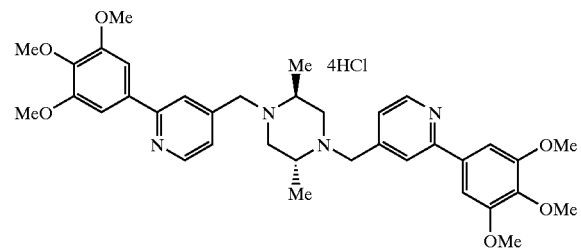

4-Chloromethyl-2-(3,4,5-trimethoxyphenyl)pyridine (123 mg) and trans-2,5-dimethylpiperazine (23 mg) were reacted in the same manner as in Example 1 to obtain the title compound as a hydrochloride.

Yield: 117 mg (93%).

$^1$H-NMR (measured as a free base, 400 MHz, CDCl$_3$) δ: 1.07(d,6H,J=6.1 Hz), 2.02(t,2H,J=10.5 Hz), 2.46–2.49(m, 2H), 2.67(dd,2H,J=11.2 Hz,2.6 Hz), 3.16(d,2H,J=14.4 Hz), 3.91(s,6H), 3.97(s,12H), 4.10(d,2H,J=14.3 Hz), 7.24(s,4H), 7.26(d,2H,J=5.3 Hz), 7.63(s,2H), 8.60(d,2H,J=5.1 Hz). m/z (EI): 628 [M$^+$].

EXAMPLE 3

Synthesis of N,N'-bis[[2-(3,4,5-trimethoxyphenyl)pyridin-4-yl]methyl]-2-hydroxymethylpiperazine dimaleate:

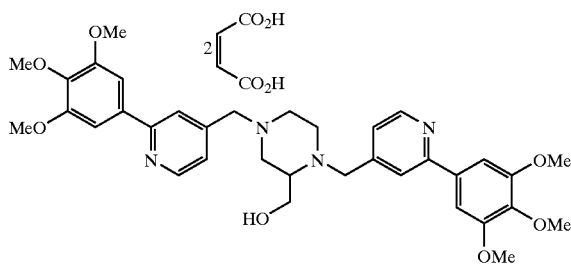

4-Chloromethyl-2-(3,4,5-trimethoxyphenyl)pyridine (1.44 g) and 2-hydroxymethylpiperazine (463 mg) were reacted in the same manner as in Example 1 to obtain the title compound as a maleate.

Yield: 116 mg (19%).

$^1$H-NMR (measured as a maleate, 400 MHz, DMSO-d$_6$) δ: 2.37–2.79(m,7H), 3.57–3.62(m,4H), 3.78(s,6H), 3.89(s, 12H), 4.05–4.11(m,2H), 6.64(s,4H), 7.23(d,1H,J=5.1 Hz), 7.26(d,1H,J=4.6 Hz), 7.34(s,2H), 7.34(s,2H), 7.76(s,1H), 7.78(s,1H), 8.52(d,1H,J=6.3 Hz), 8.53(d,1H,J=5.4 Hz). m/z (EI): 630 [M$^+$].

PREPARATION EXAMPLE 4

Synthesis of N-(2-nitrobenzenesulfonyl)glycine methyl ester

Glycine methyl ester hydrochloride (15.0 g) was dissolved in dichloromethane, and to the solution triethylamine (26.48 g) was added at 0° C. A solution of 2-nitrobenzenesulfonyl chloride (23.57 g) in dichloromethane (50 mL) was then gradually added dropwise. After the mixture was stirred at room temperature for 2 hours, the reaction mixture was concentrated under reduced pressure, and ethyl acetate was added to the residue. The resultant mixture was washed with 2 M hydrochloric acid, water and saturated brine, dried over anhydrous sodium sulfate and concentrated under reduced pressure. The resultant crystals were recrystallized from ethyl acetate-hexane to obtain the title compound.

Yield: 26.20 g (90%).

$^1$H-NMR (400 MHz, CDCl$_3$) δ: 3.61(s,3H), 4.02(d,2H,J= 5.9 Hz), 6.07(br,1H), 7.73–7.77(m,2H), 7.92–7.95(m,1H), 8.07–8.11(m,1H).

PREPARATION EXAMPLE 5

Synthesis of N-(2-nitrobenzenesulfonyl)-N-[[2-(3,4,5-trimethoxyphenyl)pyridin-4-yl]methyl]glycine methyl ester N-(2-Nitrobenzenesulfonyl)glycine methyl ester (5.60 g) was dissolved in acetonitrile (100 mL), and to the solution potassium carbonate (3.10 g) and potassium iodide (2.29 g) were added. To the mixture, 4-chloromethyl-2-(3,4,5-trimethoxyphenyl)pyridine (6.00 g) was then added, and the resultant mixture was stirred at 80° C. for 1 hour. The reaction mixture was concentrated under reduced pressure, ethyl acetate was added to the residue, and the resultant mixture was washed with a saturated aqueous solution of sodium hydrogencarbonate, water and saturated brine, dried over anhydrous sodium sulfate and concentrated under reduced pressure. The residue was purified by column chromatography on silica gel (chloroform:methanol=50:1) to obtain the title compound.

Yield: 11.35 g (theoretical amount).

$^1$H-NMR (400 MHz, CDCl$_3$) δ: 3.63(s,3H), 3.90(s,3H), 3.97(s,6H), 4.13(s,2H), 4.75(s,2H), 7.13(d,1H,J=3.5 Hz), 7.20(s,2H), 7.60(s,1H), 7.65–7.73(m,3H), 8.07(dd,1H,J=8.8 Hz,1.6 Hz), 8.61(d,1H,J=5.1 Hz)

PREPARATION EXAMPLE 6

Synthesis of N-[[2-(3,4,5-trimethoxyphenyl)pyridin-4-yl]methyl]glycine methyl ester N-(2-Nitrobenzenesulfonyl)-N-[[2-(3,4,5-trimethoxyphenyl)pyridin-4-yl]methyl]glycine methyl ester (11.35 g) was dissolved in acetonitrile (30 mL), and to the solution potassium carbonate (3.39 g) was added. Thiophenol (2.37 g) was then added to the mixture, and the resultant mixture was stirred overnight at room temperature. Ethyl acetate was added to the reaction mixture, and the resultant mixture was washed with a saturated aqueous solution of sodium hydrogencarbonate, water and saturated brine, dried over anhydrous sodium sulfate and concentrated under reduced pressure. The residue was then purified by column chromatography on silica gel (chloroform:methanol=20:1) to obtain the title compound.

Yield: 6.54 g (92%).

$^1$H-NMR (400 MHz, CDCl$_3$) δ: 3.46(s,2H), 3.74(s,3H), 3.90(s,5H), 3.97(s,6H), 7.24(s,2H), 7.25(d,1H,J=4.1 Hz), 7.67(s,1H), 8.65(d,1H,J=4.9 Hz).

PREPARATION EXAMPLE 7

Synthesis of N-(2-hydroxyethyl)-N-[[2-(3,4,5-trimethoxy-phenyl)pyridin-4-yl]methyl]amine:

N-[[2-(3,4,5-Trimethoxyphenyl)pyridin-4-yl]methyl]-glycine methyl ester (6.54 g) was dissolved in THF (80 mL), and to the solution lithium aluminum hydride (717 mg) was gradually added portionwise at 0° C. under an argon atmosphere, and the mixture was stirred for 4 hours. A small amount of water was added to the reaction mixture. When bubbling ended, sodium sulfate was excessively added. The reaction mixture was filtered through celite, and the filtrate was concentrated under reduced pressure, and the residue was purified by column chromatography on silica gel (chloroform:methanol=20:1) to obtain the title compound.

Yield: 5.03 g (84%).

$^1$H-NMR (400 MHz, CDCl$_3$) δ: 2.14(br,2H), 2.83(t,2H, J=5.1 Hz), 3.71(t,2H,J=5.1 Hz), 3.89(s,2H), 3.90(s,3H), 3.96(s,6H), 7.19(d,1H,J=4.9 Hz), 7.23(s,2H), 7.64(s,1H), 8.60(d,1H,J=5.1 Hz).

PREPARATION EXAMPLE 8

Synthesis of N-[2-(tert-butyldimethylsilyloxy)ethyl]-N-[[2-(3,4,5-trimethoxyphenyl)pyridin-4-yl]methyl]amine N-(2-Hydroxyethyl)-N-[[2-(3,4,5-trimethoxyphenyl)-pyridin-4-yl]methyl]amine (5.0 g) was dissolved in acetonitrile (100 mL), and to the solution triethylamine (2.22 g) and 4-(dimethylamino)pyridine (250 mg) were added, and tert-butylchlorodimethylsilane (3.08 g) was then added. The mixture was stirred at 50° C. for 4 hours. The reaction, the reaction mixture was concentrated under reduced pressure, ethyl acetate was added to the residue, and the mixture was washed with water and saturated brine, dried over anhydrous sodium sulfate and concentrated under reduced pressure. The residue was purified by column chromatography on silica gel (chloroform:methanol=30:1) to obtain the title compound.

Yield: 6.89 g (theoretical amount)

$^1$H-NMR (400 MHz, CDCl$_3$) δ: 0.07(s,6H), 0.90(s,9H), 1.93(br,1H), 2.76(t,2H,J=5.1 Hz), 3.77(t,2H,J=5.1 Hz), 3.90 (s,5H), 3.97(s,6H), 7.21(d,1H,J=4.7 Hz), 7.24(s,2H), 7.66(s,1H), 8.60(d,1H,J=4.9 Hz).

PREPARATION EXAMPLE 9

Synthesis of N-[2-(tert-butyldimethylsilyloxy) ethyl]-N-[[2-(3,4,5-trimethoxyphenyl)pyridin-4-yl] methyl]-Nα-(9-fluorenylmethoxycarbonyl)glycine amide N-[2-(tert-Butyldimethylsilyloxy)ethyl]-N-[[2-(3,4,5-trimethoxyphenyl)pyridin-4-yl]methyl]amine (3.40 g), N-(9-fluorenylmethoxycarbonyl)glycine (2.34 g), diisopropylethylamine (1.03 g) and 4-(dimethylamino)pyridine (961 mg) were dissolved in acetonitrile (40 mL), and to the solution HBTU (3.13 g) was added, and the mixture was stirred at room temperature for 10 minutes. The reaction mixture was concentrated under reduced pressure, ethyl acetate was added to the residue, and the mixture was washed with water and saturated brine, dried over anhydrous sodium sulfate and then concentrated under reduced pressure. The residue was purified by column chromatography on silica gel (n-hexane:ethyl acetate=1:1) to obtain the title compound.

Yield: 5.15 g (92%).

$^1$H-NMR (400 MHz, CDCl$_3$) δ: 0.04(s,6H), 0.87(s,9H), 3.43(t,2H,J=5.1 Hz), 3.75(t,2H,J=5.1 Hz), 3.90(s,3H), 3.95 (s,6H), 4.27(d,1H,J=4.5 Hz), 4.34–4.39(m,3H), 4.75(s,2H), 5.83(br,1H), 7.09(d,1H,J=4.1 Hz), 7.19(s,2H), 7.30(t,2H,J= 7.4 Hz), 7.39(t,2H,J=7.4 Hz), 7.58(s,1H), 7.61(d,2H,J=7.6 Hz), 7.76(d,2H,J=7.6 Hz), 8.61(d,1H,J=5.1 Hz).

PREPARATION EXAMPLE 10

Synthesis of N-[2-(tert-butyldimethylsilyloxy) ethyl]-N-[[2-(3,4,5-trimethoxyphenyl)pyridin-4-yl] methyl]glycine amide N-[2-(tert-butyldimethylsilyloxy)ethyl]-N-[[2-(3,4,5-trimethoxyphenyl)pyridin-4-yl]methyl]-Nα-(9-fluorenylmethoxycarbonyl)glycine amide (5.15 g) was dissolved in a 20% acetonitrile solution (40 mL) of piperidine, and the solution was stirred at room temperature for 4 hours. Ethyl acetate was added to the reaction mixture, and the mixture was washed with water and saturated brine, dried over anhydrous sodium sulfate and then concentrated under reduced pressure. The residue was purified by column chromatography on silica gel (chloroform:methanol=20:1) to obtain the title compound.

Yield: 2.76 g (78%).

$^1$H-NMR (400 MHz, CDCl$_3$) δ: 0.04(s,6H), 0.88(s,9H), 1.67 (br,2H), 3.38(t,2H,J=5.2 Hz), 3.70(s,2H), 3.72(t,2H,J= 5.2 Hz), 3.90(s,3H), 3.96(s,6H), 4.73(s,2H), 7.08(d,1H,J= 4.1 Hz), 7.20(s,2H), 7.50(s,1H), 8.60(d,1H,J=5.1 Hz).

PREPARATION EXAMPLE 11

Synthesis of N-[2-(tert-butyldimethylsilyloxy) ethyl]-N-[[2-(3,4,5-trimethoxyphenyl)pyridin-4-yl] methyl]-Nα-(2-nitrobenzenesulfonyl)glycine amide N-[2-(tert-Butyldimethylsilyloxy)ethyl]-N-[[2-(3,4,5-trimethoxyphenyl)pyridin-4-yl]methyl]glycine amide (2.52 g) was treated in the same manner as in Preparation Example 4 to obtain the title compound.

Yield: 3.41 g (98%).

$^1$H-NMR (400 MHz, CDCl$_3$) δ: 0.00(s,6H), 0.83(s,9H), 3.39(t,2H,J=4.8 Hz), 3.47(d,2H,J=7.0 Hz), 3.70(t,2H,J=4.8 Hz), 3.89(s,3H), 3.95(s,6H), 4.60(s,2H), 6.50(br,1H), 6.93 (d,1H,J=4.9 Hz), 7.18(s,2H), 7.44(s,1H), 7.61–7.67(m,2H), 7.81(dd,1H,J=7.5 Hz,1.7 Hz), 8.05(dd,1H,J=7.7 Hz,2.0 Hz), 8.54(d,1H,J=4.1 Hz).

PREPARATION EXAMPLE 12

Synthesis of N-[2-hydroxyethyl]-N-[[2-(3,4,5-trimethoxy-phenyl)pyridin-4-yl]methyl]-Nα-(2-nitrobenzenesulfonyl)-glycine amide N-[2-(tert-Butyldimethylsilyloxy)ethyl]-N-[[2-(3,4,5-trimethoxyphenyl)pyridin-4-yl]methyl]-Nα-(2-nitrobenzenesulfonyl)glycine amide (3.41 g) was dissolved in THF, and to the solution a THF solution (6.1 mL) of 1.0 M tetrabutylammonium fluoride was added, and the mixture was stirred at room temperature for 4 hours. The reaction mixture was concentrated under reduced pressure, and ethyl acetate was added to the residue. The mixture was washed with water and saturated brine, dried over anhydrous sodium sulfate and then concentrated under reduced pressure. The residue was purified by column chromatography on silica gel (chloroform:methanol=10:1) to obtain the title compound.

Yield: 2.22 g (78%).

$^1$H-NMR (400 MHz, CDCl$_3$) δ: 3.38(br,2H), 3.55(br,2H), 3.71(br,2H), 3.88(s,3H), 3.93(s,6H), 4.56(s,2H), 6.89(d,1H, J=4.9 Hz), 7.19(s,2H), 7.46(s,1H), 7.50–7.63(m,2H), 7.78 (d,1H,J=7.4 Hz), 8.04(d,1H,J=7.4 Hz), 8.49(d,1H,J=4.7 Hz).

PREPARATION EXAMPLE 13

Synthesis of 1-(2-nitrobenzenesulfonyl)-3-oxo-4-[[2-(3,4,5-trimethoxyphenyl)pyridin-4-yl]methyl] piperazine N-(2-Hydroxyethyl)-N-[[2-(3,4,5-trimethoxy-phenyl) pyridin-4-yl]methyl]-Nα-(2-nitrobenzenesulfonyl)-glycine amide (2.22 g) was dissolved in THF, and to the solution triphenylphosphine (1.55 g) was added. DEAD (1.03 g) was slowly added to the mixture at room temperature, and the resultant mixture was stirred overnight at room temperature under an argon atmosphere. After the reaction mixture was concentrated under reduced pressure, ethyl acetate was added to the residue. The mixture was washed with a saturated aqueous solution of sodium hydrogencarbonate, water and saturated brine, dried over anhydrous sodium sulfate and then concentrated under reduced pressure. The residue was purified by column chromatography on silica gel (ethyl acetate) to obtain the title compound.

Yield: 2.01 g (94%).

$^1$H-NMR (400 MHz, CDCl$_3$) δ: 3.42(t,2H,J=5.2 Hz), 3.67(t,2H,J=5.2 Hz), 3.90(s,3H), 3.96(s,6H), 4.07(s,2H), 4.67(s,2H), 7.05(d,1H,J=4.6 Hz), 7.20(s,2H), 7.51(s,1H), 7.63(d,1H,J=2.0 Hz), 7.69–7.76(m,2H), 8.03(d,1H,J=2.2 Hz), 8.61(d,1H,J=5.1 Hz).

PREPARATION EXAMPLE 14

Synthesis of 2-oxo-1-[[2-(3,4,5-trimethoxyphenyl)pyridin-4-yl]methyl]piperazine 1-(2-Nitrobenzenesulfonyl)-3-oxo-4-[[2-(3,4,5-trimethoxyphenyl)pyridin-4-yl]methyl]piperazine (1.83 g) was treated in the same manner as in Preparation Example 6 to obtain the title compound.

Yield: 118 mg (10%).

1H-NMR (400 MHz, CDCl$_3$) δ: 1.82(br,1H), 3.09(t,2H, J=5.4 Hz), 3.29(t,2H,J=5.4 Hz), 3.65(s,2H), 3.90(s,6H), 3.96(s,3H), 4.67(s,2H), 7.12(d,1H,J=4.9 Hz), 7.21(s,2H), 7.55(s,1H), 8.63(d,1H,J=5.1 Hz).

EXAMPLE 4

Synthesis of 2-oxo-N,N'-bis[[2-(3,4,5-trimethoxyphenyl)-pyridin-4-yl]methyl]piperazine 2.5 hydrochloride

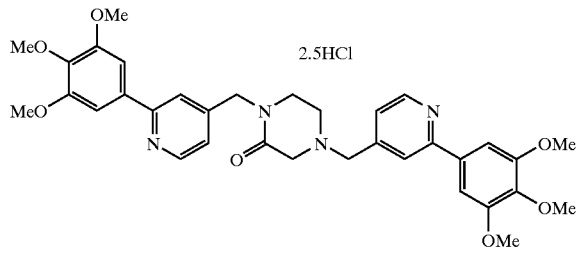

2-Oxo-1-[[2-(3,4,5-trimethoxyphenyl)pyridin-4-yl]methyl]piperazine (62 mg) was dissolved in acetonitrile (5 mL), and to the solution potassium carbonate (24 mg), potassium iodide (29 mg) and 4-chloromethyl-2-(3,4,5-trimethoxyphenyl)pyridine (51 mg) were added, and the mixture was stirred at 80° C. for 1 hour. The reaction mixture was concentrated under reduced pressure, ethyl acetate was added to the residue, and the resultant mixture was washed with a saturated aqueous solution of sodium hydrogencarbonate, water and saturated brine, dried over anhydrous sodium sulfate and concentrated under reduced pressure. The resultant oil was purified by preparative TLC on silica gel (chloroform:methanol=25:1) to obtain the title compound as a hydrochloride.

Yield: 92 mg (87%).

1H-NMR (measured as a free base, 400 MHz, CDCl$_3$) δ: 2.73(t,2H,J=5.1 Hz), 3.32(t,2H,J=5.1 Hz), 3.34(s,2H), 3.65 (s,2H), 3.90(s,6H), 3.96(s,12H), 4.67(s,2H), 7.11(d,1H,J= 4.9 Hz), 7.22(br,5H), 7.55(s,1H), 7.61(s,1H), 8.63–8.64(m, 2H).

m/z (EI): 614 [M$^+$].

PREPARATION EXAMPLE 15

Synthesis of N-[2-(tert-butyldimethylsilyloxy)ethyl]-N-[[2-(3,4,5-trimethoxyphenyl)pyridin-4-yl]methyl]-Nα-(9-fluorenylmethoxycarbonyl)-L-alanine amide N-[2-(tert-Butyldimethylsilyloxy)ethyl]-N-[[2-(3,4,5-trimethoxyphenyl)pyridin-4-yl]methyl]amine (756 mg) and N-(9-fluorenylmethoxycarbonyl)-L-alanine (544 mg) were treated in the same manner as in Preparation Example 9 to obtain the title compound. Since this compound was unable to be isolated from impurities, it was used in the next reaction without purifying it as it is.

PREPARATION EXAMPLE 16

Synthesis of N-[2-(tert-butyldimethylsilyloxy)ethyl]-N-[[2-(3,4,5-trimethoxyphenyl)pyridin-4-yl]methyl]-L-alanine amide The whole amount of the reaction mixture obtained in Preparation Example 15 was treated in the same manner as in Preparation Example 10 to obtain the title compound.

Yield: 340 mg (39% by 2 steps).

PREPARATION EXAMPLE 17

Synthesis of N-[2-(tert-butyldimethylsilyloxy)ethyl]-N-[[2-(3,4,5-trimethoxyphenyl)pyridin-4-yl]methyl]-Nα-(2-nitrobenzenesulfonyl)-L-alanine amide N-[2-(tert-Butyldimethylsilyloxy)ethyl]-N-[[2-(3,4,5-trimethoxyphenyl)pyridin-4-yl]methyl]-L-alanine amide (340 mg) was treated in the same manner as in Preparation Example 4 to obtain the title compound.

Yield: 303 mg (65%).

PREPARATION EXAMPLE 18

Synthesis of N-(2-hydroxyethyl)-N-[[2-(3,4,5-trimethoxy-phenyl)pyridin-4-yl]methyl]-Nα-(2-nitrobenzenesulfonyl)-L-alanine amide N-[2-(tert-Butyldimethylsilyloxy)ethyl]-N-[[2-(3,4,5-trimethoxyphenyl)pyridin-4-yl]methyl]-Nα-(2-nitrobenzenesulfonyl)-L-alanine amide (669 mg) was treated in the same manner as in Preparation Example 12 to obtain the title compound.

Yield: 546 mg (98%).

PREPARATION EXAMPLE 19

Synthesis of (3S)-3-methyl-4-(2-nitrobenzenesulfonyl)-2-oxo-1-[[2-(3,4,5-trimethoxyphenyl)pyridin-4-yl]methyl]piperazine N-(2-Hydroxyethyl)-N-[[2-(3,4,5-trimethoxyphenyl)-pyridin-4-yl]methyl]-Nα-(2-nitrobenzenesulfonyl)-L-alanine amide (546 mg) was treated in the same manner as in Preparation Example 13 to obtain the title compound. Since removal of by-products could not be completely conducted, this compound was used in the next reaction without conducting further purification.

PREPARATION EXAMPLE 20

Synthesis of (3S)-3-methyl-2-oxo-1-[[2-(3,4,5-trimethoxy-phenyl)pyridin-4-yl]methyl]piperazine The whole amount of the reaction mixture obtained in Preparation Example 19 was treated in the same manner as in Preparation Example 6 to obtain the title compound.

Yield: 174 mg (50% by 2 steps).

1H-NMR (400 MHz, CDCl$_3$) δ: 1.47(d,3H,J=6.8 Hz), 1.78(br,1H), 3.02–3.09(m,1H), 3.15–3.22(m,2H), 3.39–3.45 (m,1H), 3.65(q,1H,J=6.8 Hz), 3.90(s,3H), 3.96(s,6H), 4.60 (d,1H,J=15.2 Hz), 4.70(d,1H,J=15.2 Hz), 7.10(dd,1H,J=5.0 Hz,1.5 Hz), 7.22(s,2H), 7.53(s,1H), 8.62(d,1H,J=4.9 Hz).

EXAMPLE 5

Synthesis of (3S)-3-methyl-2-oxo-N,N'-bis[[2-(3,4,5-trimethoxyphenyl)pyridin-4-yl]methyl]piperazine 2.5 hydrochloride

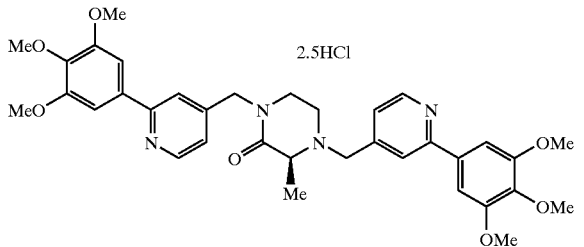

(3S)-3-Methyl-2-oxo-1-[[2-(3,4,5-trimethoxy-phenyl)pyridin-4-yl]methyl]piperazine (80 mg) and 4-chloromethyl-2-(3,4,5-trimethoxyphenyl)pyridine (63 mg) were reacted in the same manner as in Example 4 to obtain the title compound as a hydrochloride.

Yield: 124 mg (92%).

$^1$H-NMR (measured as a free base, 400 MHz, CDCl$_3$) δ: 1.56(d,3H,J=6.6 Hz), 2.53–2.59(m,1H), 2.95–2.99(m,1H), 3.21–3.33(m,2H), 3.43(q,1H,J=6.8 Hz), 3.52(d,1H,J=14.4 Hz), 3.90(s,6H), 3.95(s,6H), 3.95(s,7H), 4.58(d,1H,J=15.4 Hz), 4.75(d,1H,J=15.2 Hz), 7.10(d,1H,J=4.7 Hz), 7.22(s, 2H), 7.23(m,3H), 7.54(s,1H), 7.62(s,1H), 8.61(d,1H,J=5.7 Hz), 8.63(d,1H,J=5.9 Hz).

m/z (EI): 628 [M$^+$].

PREPARATION EXAMPLE 21

Synthesis of N-[2-(tert-butyldimethylsilyloxy)ethyl]-N-[[2-(3,4,5-trimethoxyphenyl)pyridin-4-yl]methyl]-Nα-(9-fluorenylmethoxycarbonyl)-L-valine amide N-[2-(tert-Butyldimethylsilyloxy)ethyl]-N-[[2-(3,4,5-trimethoxyphenyl)pyridin-4-yl]methyl]amine (679 mg) and N-(9-fluorenylmethoxycarbonyl)-L-valine (865 mg) were treated in the same manner as in Preparation Example 9 to obtain the title compound.

Yield: 1.11 g (74%).

PREPARATION EXAMPLE 22

Synthesis of N-[2-(tert-butyldimethylsilyloxy)ethyl]-N-[[2-(3,4,5-trimethoxyphenyl)pyridin-4-yl]methyl]-L-valine amide N-[2-(tert-Butyldimethylsilyloxy)ethyl]-N-[[2-(3,4,5-trimethoxyphenyl)pyridin-4-yl]methyl]-Nα-(9-fluorenylmethoxycarbonyl)-L-valine amide (1.11 g) was treated in the same manner as in Preparation Example 10 to obtain the title compound.

Yield: 705 mg (90%).

PREPARATION EXAMPLE 23

Synthesis of N-[2-(tert-butyldimethylsilyloxy)ethyl]-N-[[2-(3,4,5-trimethoxyphenyl)pyridin-4-yl]methyl]-Nα-(2-nitrobenzenesulfonyl)-L-valine amide N-[2-(tert-Butyldimethylsilyloxy)ethyl]-N-[[2-(3,4,5-trimethoxyphenyl)pyridin-4-yl]methyl]-L-valine amide (705 mg) was treated in the same manner as in Preparation Example 4 to obtain the title compound.

Yield: 877 mg (92%).

PREPARATION EXAMPLE 24

Synthesis of N-(2-hydroxyethyl)-N-[[2-(3,4,5-trimethoxy-phenyl)pyridin-4-yl]methyl]-Nα-(2-nitrobenzenesulfonyl)-L-valine amide N-[2-(tert-Butyldimethylsilyloxy)ethyl]-N-[[2-(3,4,5-trimethoxyphenyl)pyridin-4-yl]methyl]-Nα-(2-nitrobenzenesulfonyl)-L-valine amide (877 mg) was treated in the same manner as in Preparation Example 12 to obtain the title compound.

Yield: 689 mg (95%).

PREPARATION EXAMPLE 25

Synthesis of (3S)-3-isopropyl-4-(2-nitrobenzenesulfonyl)-2-oxo-1-[[2-(3,4,5-trimethoxyphenyl)pyridin-4-yl]methyl]-piperazine N-(2-Hydroxyethyl)-N-[[2-(3,4,5-trimethoxyphenyl)-pyridin-4-yl]methyl]-Nα-(2-nitrobenzenesulfonyl)-L-valine amide (546 mg) was treated in the same manner as in Preparation Example 13 to obtain the title compound. Since removal of by-products could not be completely conducted, this compound was used in the next reaction without conducting further purification.

PREPARATION EXAMPLE 26

Synthesis of (3S)-3-isopropyl-2-oxo-1-[[2-(3,4,5-trimethoxyphenyl)pyridin-4-yl]methyl]piperazine The whole amount of the reaction mixture obtained in Preparation Example 25 was treated in the same manner as in Preparation Example 6 to obtain the title compound.

Yield: 365 mg (79% by 2 steps).

$^1$H-NMR (400 MHz, CDCl$_3$) δ: 0.97(d,3H,J=6.8 Hz), 1.05(d,3H,J=7.0 Hz), 1.63(br,1H), 2.56–2.64(m,1H), 2.99–3.31(m,3H), 3.41–3.47(m,2H), 3.90(s,3H), 3.95(s,6H), 4.48(d,1H,J=15.4 Hz), 4.90(d,1H,J=15.4 Hz), 7.10(dd,1H, J=4.9 Hz,1.2 Hz), 7.21(s,2H), 7.53(s,1H), 8.61(d,1H,J=5.1 Hz).

EXAMPLE 6

Synthesis of (3S)-3-isopropyl-2-oxo-N,N'-bis[[2-(3,4,5-trimethoxyphenyl)pyridin-4-yl]methyl]piperazine sesqui-hydrochloride

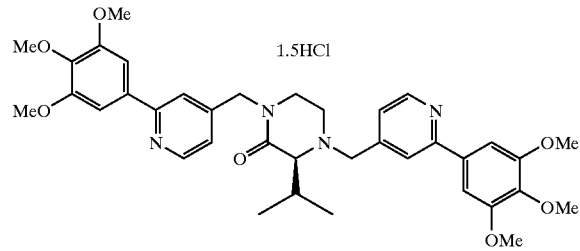

(3S)-3-Isopropyl-2-oxo-1-[[2-(3,4,5-trimethoxy-phenyl)pyridin-4-yl]methyl]piperazine (80 mg) and 4-chloromethyl-2-(3,4,5-trimethoxyphenyl)pyridine (59 mg) were reacted in the same manner as in Example 4 to obtain the title compound as a hydrochloride.

Yield: 98 mg (75%).

$^1$H-NMR (measured as a free base, 400 MHz, CDCl$_3$) δ: 1.13(d,3H,J=6.8 Hz), 1.22(d,3H,J=6.8 Hz), 2.23–2.27(m, 1H), 2.60–2.64(m,1H), 3.03–3.35(m,4H), 3.65(d,1H,J=14.8 Hz), 3.90(s,3H), 3.91(s,3H), 3.95(s,6H), 3.96(s,6H), 3.96(d, 1H,J=14.8 Hz), 4.48(d,1H,J=15.2 Hz), 4.92(d,1H,J=15.2 Hz), 7.12(d,1H,J=4.9 Hz), 7.21–7.24(m,5H), 7.56(s,1H), 7.65(s,1H), 8.60(d,1H,J=4.9 Hz), 8.63(d,1H,J=5.1 Hz).

m/z (EI): 656 [M+].

PREPARATION EXAMPLE 27

Synthesis of N-[2-(tert-butyldimethylsilyloxy) ethyl]-N-[[2-(3,4,5-trimethoxyphenyl)pyridin-4-yl] methyl]-Nα-(9-fluorenylmethoxycarbonyl)-D-valine amide N-[2-(tert-Butyldimethylsilyloxy)ethyl]-N-[[2-(3,4,5-trimethoxyphenyl)pyridin-4-yl]methyl]amine (1.27 g) and N-(9-fluorenylmethoxycarbonyl)-D-valine (1.00 g) were treated in the same manner as in Preparation Example 9 to obtain the title compound. Since impurities were unable to be removed from this compound, the compound was provided to the next step without purifying it.

PREPARATION EXAMPLE 28

Synthesis of N-[2-(tert-butyldimethylsilyloxy) ethyl]-N-[[2-(3,4,5-trimethoxyphenyl)pyridin-4-yl] methyl]-D-valine amide Crude N-[2-(tert-butyldimethylsilyloxy)ethyl]-N-[[2-(3, 4,5-trimethoxyphenyl)pyridin-4-yl]methyl]-Nα-(9-fluorenylmethoxycarbonyl)-D-valine amide obtained in Preparation Example 27 was treated in the same manner as in Preparation Example 10 to obtain the title compound.

Yield: 1.00 g (64% by 2 steps).

PREPARATION EXAMPLE 29

Synthesis of N-[2-(tert-butyldimethylsilyloxy) ethyl]-N-[[2-(3,4,5-trimethoxyphenyl)pyridin-4-yl] methyl]-Nα-(2-nitrobenzenesulfonyl)-D-valine amide N-[2-(tert-Butyldimethylsilyloxy)ethyl]-N-[[2-(3,4,5-trimethoxyphenyl)pyridin-4-yl]methyl]-D-valine amide (1.00 g) was treated in the same manner as in Preparation Example 4 to obtain the title compound.

Yield: 1.36 g (94%).

PREPARATION EXAMPLE 30

Synthesis of N-(2-hydroxyethyl)-N-[[2-(3,4,5-trimethoxy-phenyl)pyridin-4-yl]methyl]-Nα-(2-nitrobenzenesulfonyl)-D-valine amide N-[2-(tert-Butyldimethylsilyloxy)ethyl]-N-[[2-(3,4,5-trimethoxyphenyl)pyridin-4-yl]methyl]-Nα-(2-nitrobenzenesulfonyl)-D-valine amide (1.36 g) was treated in the same manner as in Preparation Example 12 to obtain the title compound.

Yield: 1.08 g (94%).

PREPARATION EXAMPLE 31

Synthesis of (2R)-2-isopropyl-1-(2-nitrobenzenesulfonyl)-3-oxo-4-[[2-(3,4,5-trimethoxyphenyl)pyridin-4-yl]methyl]-piperazine N-(2-Hydroxyethyl)-N-[[2-(3,4,5-trimethoxyphenyl)-pyridin-4-yl]methyl]-Nα-(2-nitrobenzenesulfonyl)-D-valine amide (258 mg) was treated in the same manner as in Preparation Example 13 to obtain the title compound. Since removal of by-products could not be completely conducted, this compound was used in the next reaction without conducting further purification.

PREPARATION EXAMPLE 32

Synthesis of (3R)-3-isopropyl-2-oxo-1-[[2-(3,4,5-trimethoxyphenyl)pyridin-4 -yl]methyl]piperazine The whole amount of the reaction mixture obtained in Preparation Example 31 was treated in the same manner as in Preparation Example 6 to obtain the title compound.

Yield: 109 mg (63% by 2 steps).

1H-NMR (400 MHz, CDCl3) δ: 1.01(d,3H, J=6.6 Hz), 1.08(d,3H,J=7.0 Hz), 2.58–2.70(m,1H), 3.05–3.30(m,3H), 3.45–3.57(m,2H), 3.93(s,3H), 3.98(s,6H), 4.51(d,1H,J=15.4 Hz), 4.92(d,1H,J=15.4 Hz), 7.12(d,1H,J=5.1 Hz), 7.24(s, 2H), 7.56(s,1H), 8.64(d,1H,J=4.9 Hz).

EXAMPLE 7

Synthesis of (3R)-3-isopropyl-2-oxo-N,N'-bis[[2-(3, 4,5-trimethoxyphenyl)pyridin-4-yl]methyl] piperazine tri-hydrochloride

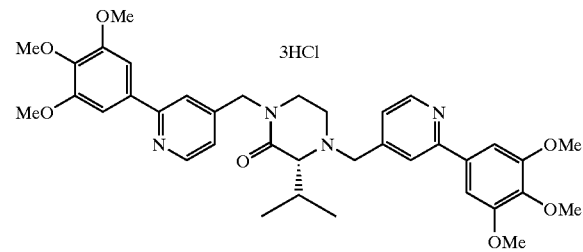

(3R)-3-Isopropyl-2-oxo-1-[[2-(3,4,5-trimethoxy-phenyl) pyridin- 4-yl]methyl]piperazine (109 mg) and 4-chloromethyl-2-(3,4,5-trimethoxyphenyl)pyridine (104 mg) were reacted in the same manner as in Example 4 to obtain the title compound as a hydrochloride.

Yield: 58 mg (50%).

1H-NMR (measured as a free base, 400 MHz, CDCl13) δ: 1.14(d,3H,J=7.0 Hz), 1.23(d,3H,J=6.8 Hz), 2.20–2.35(m, 1H), 2.58–2.70(m,1H), 3.03–3.45(m,4H), 3.67(d,1H,J=14.8 Hz), 3.90–3.91(m,6H), 3.96–3.97(m,15H), 7.13–7.15(m, 1H), 7.24(s,5H), 7.59(s,1H), 7.67(s,1H), 8.61(d,1H,J=5.1 Hz), 8.64(d,1H,J=5.1 Hz).

m/z (EI): 656 [M+].

PREPARATION EXAMPLE 33

Synthesis of N-[2-(tert-butyldimethylsilyloxy) ethyl]-N-[[2-(3,4,5-trimethoxyphenyl)pyridin-4-yl] methyl]-Nα-(9-fluorenylmethoxycarbonyl)-L-leucine amide N-[2-(tert-Butyldimethylsilyloxy)ethyl]-N-[[2-(3,4,5-trimethoxyphenyl)pyridin-4-yl]methyl]amine (1.40 g) and N-(9-fluorenylmethoxycarbonyl)-L-leucine (1.16 g) were treated in the same manner as in Preparation Example 9 to obtain the title compound.

Yield: 2.32 g (93%).

PREPARATION EXAMPLE 34

Synthesis of N-[2-(tert-butyldimethylsilyloxy) ethyl]-N-[[2-(3,4,5-trimethoxyphenyl)pyridin-4-yl] methyl]-L-leucine amide N-[2-(tert-Butyldimethylsilyloxy)ethyl]-N-[[2-(3,4,5 -trimethoxyphenyl)pyridin-4-yl]methyl]-Nα-(9- fluorenylmethoxycarbonyl)-L-leucine amide (2.32 g) was treated in the same manner as in Preparation Example 10 to obtain the title compound.

Yield: 1.57 g (96%).

PREPARATION EXAMPLE 35

Synthesis of N-[2-(tert-butyldimethylsilyloxy) ethyl]-N-[[2-(3,4,5-trimethoxyphenyl)pyridin-4-yl] methyl]-Nα-(2-nitrobenzenesulfonyl)-L-leucine amide N-[2-(tert-Butyldimethylsilyloxy)ethyl]-N-[[2-(3,4,5-trimethoxyphenyl)pyridin-4-yl]methyl]-L-leucine amide (1.57 g) was treated in the same manner as in Preparation Example 4 to obtain the title compound.

Yield: 2.05 g (98%).

PREPARATION EXAMPLE 36

Synthesis of N-(2-hydroxyethyl)-N-[[2-(3,4,5-trimethoxy-phenyl)pyridin-4-yl]methyl]-Nα-(2-nitrobenzenesulfonyl)-L-leucine amide N-[2-(tert-Butyldimethylsilyloxy)ethyl]-N-[[2-(3,4,5-trimethoxyphenyl)pyridin-4-yl]methyl]-Nα-(2-nitrobenzenesulfonyl)-L-leucine amide (2.05 g) was treated in the same manner as in Preparation Example 12 to obtain the title compound.

Yield: 1.61 g (93%).

PREPARATION EXAMPLE 37

Synthesis of (3S)-3-(2-methylpropyl)-4-(2-nitrobenzene-sulfonyl)-2-oxo-1-[[2-(3,4,5-trimethoxyphenyl)pyridin-4-yl]methyl]piperazine N-(2-Hydroxyethyl)-N-[[2-(3,4,5-trimethoxyphenyl)-pyridin-4-yl]methyl]-Nα-(2-nitrobenzenesulfonyl)-L-leucine amide (1.57 g) was treated in the same manner as in Preparation Example 13 to obtain the title compound. Since removal of by-products could not be completely conducted, this compound was used in the next reaction without conducting further purification.

PREPARATION EXAMPLE 38

Synthesis of (3S)-3-(2-methylpropyl)-2-oxo-1-[[2-(3,4,5-trimethoxyphenyl)pyridin-4-yl]methyl] piperazine The whole amount of the reaction mixture obtained in Preparation Example 37 was treated in the same manner as in Preparation Example 6 to obtain the title compound.

Yield: 689 mg (44% by 2 steps).

$^1$H-NMR (400 MHz, CDCl$_3$) δ: 0.95(d,3H,J=6.6 Hz), 0.98(d,3H,J=6.6 Hz), 1.60(ddd,1H,J=13.7 Hz,9.9 Hz,4.2 Hz), 1.71(br,1H), 1.77–1.80(m,1H), 1.95(ddd,1H,J=13.7 Hz,9.9 Hz,4.2 Hz), 2.98–3.05(m,1H), 3.15–3.23(m,2H), 3.35–3.42(m,1H), 3.55(dd,1H,J=10.1 Hz,3.6 Hz), 3.90(s, 3H), 3.96(s,6H), 4.63(d,1H,J=15.2 Hz), 4.67(d,1H,J=15.2 Hz), 7.09(dd,1H,J=5.1 Hz,1.6 Hz), 7.21(s,2H), 7.53(d,1H, J=0.6 Hz), 8.61(dd,1H,J=5.0 Hz,0.7 Hz).

EXAMPLE 8

Synthesis of (3S)-3-(2-methylpropyl)-2-oxo-N,N'-bis[[2-(3,4,5-trimethoxyphenyl)pyridin-4-yl]methyl] piperazine 2.5 hydrochloride (3S)-3-(2-methylpropyl)-2-oxo-1-[[2-(3,4,5-trimethoxy-phenyl)pyridin-4-yl]methyl]piperazine (100 mg) and 4-chloromethyl-2-(3,4,5-trimethoxyphenyl)pyridine (71 mg) were reacted in the same manner as in Example 4 to obtain the title compound as a hydrochloride.

Yield: 58 mg (50%).

$^1$H-NMR (measured as a free base, 400 MHz, CDCl$_3$) δ: 0.90(d,3H,J=6.2 Hz), 0.97(d,3H,J=6.4 Hz), 1.78–1.81(m, 1H), 1.90–2.00(m,2H), 2.63(dt,1H,J=13.3 Hz,4.9 Hz), 3.12–3.25(m,2H), 3.30(t,1H,J=5.9 Hz), 3.37–3.42(m,1H), 3.64(d,1H,J=14.3 Hz), 3.90(s,6H), 3.96(m,13H), 4.50(d,1H, J=5.0 Hz), 4.86(d,1H,J=5.2 Hz), 7.12(d,1H,J=3.7 Hz), 7.21 (d,1H,J=5.1 Hz), 7.22(s,2H), 7.23(s,2H), 7.56(s,1H), 7.65(s, 1H), 8.61(d,1H,J=4.9 Hz), 8.64(d,1H,J=4.7 Hz).

m/z (EI): 670 [M$^+$].

PREPARATION EXAMPLE 39

Synthesis of N-[2-(tert-butyldimethylsilyloxy) ethyl]-N-[[2-(3,4,5-trimethoxyphenyl)pyridin-4-yl] methyl]-Nα-(9-fluorenylmethoxycarbonyl)-L-phenylalanine amide N-[2-(tert-Butyldimethylsilyloxy)ethyl]-N-[[2-(3,4,5-trimethoxyphenyl)pyridin-4-yl]methyl]amine (973 mg) and N-(9-fluorenylmethoxycarbonyl)-L-phenylalanine (871 mg) were treated in the same manner as in Preparation Example 9 to obtain the title compound.

Yield: 1.35 g (75%).

PREPARATION EXAMPLE 40

Synthesis of N-[2-(tert-butyldimethylsilyloxy) ethyl]-N-[[2-(3,4,5-trimethoxyphenyl)pyridin-4-yl] methyl]-L-phenylalanine amide N-[2-(tert-Butyldimethylsilyloxy)ethyl]-N-[[2-(3,4,5-trimethoxyphenyl)pyridin-4-yl]methyl]-Nα-(9-fluorenylmethoxycarbonyl)-L-phenylalanine amide (1.35 g) was treated in the same manner as in Preparation Example 10 to obtain the title compound.

Yield: 865 mg (89%).

PREPARATION EXAMPLE 41

Synthesis of N-[2-(tert-butyldimethylsilyloxy) ethyl]-N-[[2-(3,4,5-trimethoxyphenyl)pyridin-4-yl] methyl]-Nα-(2-nitrobenzenesulfonyl)-L-phenylalanine amide N-[2-(tert-Butyldimethylsilyloxy)ethyl]-N-[[2-(3,4,5-trimethoxyphenyl)pyridin-4-yl]methyl]-L-phenylalanine amide (865 mg) was treated in the same manner as in Preparation Example 4 to obtain the title compound.

Yield: 1.07 g (94%).

PREPARATION EXAMPLE 42

Synthesis of N-(2-hydroxyethyl)-N-[[2-(3,4,5-trimethoxy-phenyl)pyridin-4-yl]methyl]-Nα-(2-nitrobenzenesulfonyl)-L-phenylalanine amide N-[2-(tert-Butyldimethylsilyloxy)ethyl]-N-[[2-(3,4,5-trimethoxyphenyl)pyridin-4-yl]methyl]-Nα-(2-nitrobenzenesulfonyl)-L-phenylalanine amide (1.06 g) was treated in the same manner as in Preparation Example 12 to obtain the title compound.

Yield: 983 mg (theoretical amount).

PREPARATION EXAMPLE 43

Synthesis of (3S)-3-benzyl-4-(2-nitrobenzenesulfonyl)-2-oxo-1-[[2-(3,4,5-trimethoxyphenyl)pyridin-4-yl]methyl]-piperazine N-(2-Hydroxyethyl)-N-[[2-(3,4,5-trimethoxyphenyl)-pyridin-4-yl]methyl]-Nα-(2-nitrobenzenesulfonyl)-L-phenylalanine amide (921 mg) was treated in the same manner as in Preparation Example 13 to obtain the title compound. Since removal of by-products could not be completely conducted, this compound was used in the next reaction without conducting further purification.

PREPARATION EXAMPLE 44

Synthesis of (3S)-3-benzyl-2-oxo-1-[[2-(3,4,5-trimethoxy-phenyl)pyridin-4-yl]methyl]piperazine The whole amount of the reaction mixture obtained in Preparation Example 43 was treated in the same manner as in Preparation Example 6 to obtain the title compound.

Yield: 430 mg (69% by 2 steps).

$^1$H-NMR (400 MHz, CDCl$_{13}$) δ: 1.62(br,1H), 2.90–2.96 (m,2H), 3.09–3.17(m,2H), 3.38(dt,1H,J=10.9 Hz,4.3 Hz), 3.52(dd,1H,J=13.6 Hz,3.4 Hz), 3.74(dd,1H,J=9.8 Hz,3.5 Hz), 3.90(s,3H), 3.96(s,6H), 4.65(d,1H,J=15.2 Hz), 4.70(d,1H,J=15.2 Hz), 7.05(dd,1H,J=5.1 Hz,1.6 Hz), 7.22(s,2H), 7.25–7.34(m,5H), 7.54(s,1H), 8.61(d,1H,J=5.1 Hz).

EXAMPLE 9

Synthesis of (3S)-3-benzyl-2-oxo-N,N'-bis[[2-(3,4,5-trimethoxyphenyl)pyridin-4-yl]methyl]piperazine sesqui-hydrochloride

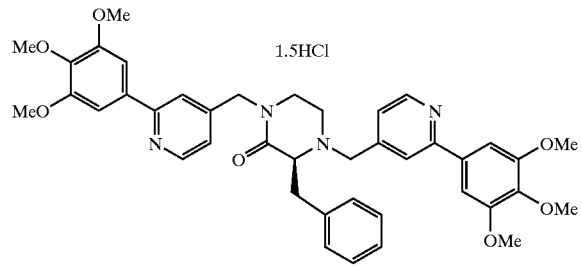

(3S)-3-benzyl-2-oxo-1-[[2-(3,4,5-trimethoxy-phenyl) pyridin-4-yl]methyl]piperazine (89 mg) and 4-chloromethyl-2-(3,4,5-trimethoxyphenyl)pyridine (59 mg) were reacted in the same manner as in Example 4 to obtain the title compound as a hydrochloride.

Yield: 102 mg (72%).

$^1$H-NMR (measured as a free base, 400 MHz, CDCl$_3$) δ: 2.52–2.58(m,1H), 3.01(dt,1H,J=12.9 Hz,4.5 Hz), 3.11–3.13 (m,2H), 3.26(dd,1H,J=14.2 Hz,4.3 Hz), 3.39(dd,1H,J=14.2 Hz,5.8 Hz), 3.51(d,1H,J=14.4 Hz),⊁3.58(t,1H,J=4.8 Hz), 3.90(s,3H), 3.91(s,3H), 3.94(s,12H), 4.13(d,1H,J=14.3 Hz), 4.39(d,1H,J=15.2 Hz), 4.87(d,1H,J=15.2 Hz), 6.79(d,1H,J= 4.1 Hz), 7.00(d,1H,J=4.7 Hz), 7.17–7.30(m,9H), 7.48(s,1H), 7.50(s,1H), 8,53(d,1H,J=5.1 Hz), 8.55(d,1H,J=5.1 Hz).

m/z (EI): 704 [M$^+$].

PREPARATION EXAMPLE 45

Synthesis of N-[2-(tert-butyldimethylsilyloxy) ethyl]-N-[[2-(3,4,5-trimethoxyphenyl)pyridin-4-yl] methyl]-Nα-(9-fluorenylmethoxycarbonyl)-Nω-trityl-L-asparagine amide N-[2-(tert-Butyldimethylsilyloxy)ethyl]-N-[[2-(3,4,5-trimethoxyphenyl)pyridin-4-yl]methyl]amine (725 mg) and N-(9-fluorenylmethoxycarbonyl)-Nω-trityl-L-asparagine (1.00 g) were treated in the same manner as in Preparation Example 9 to obtain the title compound.

Yield: 563 mg (33%).

PREPARATION EXAMPLE 46

Synthesis of N-[2-(tert-butyldimethylsilyloxy) ethyl]-N-[[2-(3,4,5-trimethoxyphenyl)pyridin-4-yl] methyl]-Nω-trityl-L-asparagine amide N-[2-(tert-Butyldimethylsilyloxy)ethyl]-N-[[2-(3,4,5-trimethoxyphenyl)pyridin-4-yl]methyl]-Nω-(9-fluorenylmethoxycarbonyl)-Nω-trityl-L-asparagine amide (563 mg) was treated in the same manner as in Preparation Example 10 to obtain the title compound.

Yield: 396 mg (90%).

PREPARATION EXAMPLE 47

Synthesis of N-[2-(tert-butyldimethylsilyloxy) ethyl]-N-[[2-(3,4,5-trimethoxyphenyl)pyridin-4-yl] methyl]-Nα-(2-nitrobenzenesulfonyl)-Nω-trityl-L-asparagine amide N-[2-(tert-Butyldimethylsilyloxy)ethyl]-N-[[2-(3,4,5-trimethoxyphenyl)pyridin-4-yl]methyl]-Nω-trityl-L-asparagine amide (396 mg) was treated in the same manner as in Preparation Example 4 to obtain the title compound.

Yield: 465 mg (95%).

PREPARATION EXAMPLE 48

Synthesis of N-(2-hydroxyethyl)-N-[[2-(3,4,5-trimethoxy-phenyl)pyridin-4-yl]methyl]-Nα-(2-nitrobenzenesulfonyl)-Nω-trityl-L-asparagine amide N-[2-(tert-Butyldimethylsilyloxy)ethyl]-N-[[2-(3,4,5-trimethoxyphenyl)pyridin-4-yl]methyl]-Nα-(2-nitrobenzenesulfonyl)-Nω-trityl-L-asparagine amide (410 mg) was treated in the same manner as in Preparation Example 12 to obtain the title compound.

Yield: 410 mg (88%).

PREPARATION EXAMPLE 49

Synthesis of (3S)-4-(2-nitrobenzenesulfonyl)-2-oxo-1-[[2-(3,4,5-trimethoxyphenyl)pyridin-4-yl]methyl]-3-[2-(tritylaminocarbonyl)methyl]piperazine N-(2-Hydroxyethyl)-N-[[2-(3,4,5-trimethoxyphenyl)-pyridin-4-yl]methyl]-Nα-(2-nitrobenzenesulfonyl)-Nω- trityl-L-asparagine amide (410 mg) was treated in the same manner as in Preparation Example 13 to obtain the title compound. Since removal of by-products could not be completely conducted, this compound was used in the next reaction without conducting further purification.

PREPARATION EXAMPLE 50

Synthesis of (3S)-2-oxo-1-[[2-(3,4,5-trimethoxyphenyl)-pyridin-4-yl]methyl]-3-[2-(tritylaminocarbonyl)methyl]-piperazine The whole amount of the reaction mixture obtained in Preparation Example 49 was treated in the same manner as in Preparation Example 6 to obtain the title compound.

Yield: 233 mg (75% by 2 steps).

$^1$H-NMR (400 MHz, CDCl$_3$) δ: 2.74(br,1H), 2.87–3.08 (m,5H), 3.35–3.39(m,1H), 3.73–3.76(m,1H), 3.89(s,3H), 3.93(s,6H), 4.45(dd,1H,J=15.3 Hz,6.5 Hz), 4.72(dd,1H,J=15.3 Hz,7.1 Hz), 7.03(d,1H,J=3.5 Hz), 7.18–7.28(m,18H), 7.47(s,1H), 8.53(d,1H,J=4.9 Hz).

PREPARATION EXAMPLE 51

Synthesis of (3S)-2-oxo-N,N'-bis[[2-(3,4,5-trimethoxy-phenyl)pyridin-4-yl]methyl]-3-[2-(tritylaminocarbonyl)-methyl]piperazine (3S)-2-Oxo-1-[[2-(3,4,5-trimethoxyphenyl)pyridin-4-yl] methyl]-3-[2-(tritylaminocarbonyl)methyl]piperazine (233 mg) and 4-chloromethyl-2-(3,4, 5-trimethoxyphenyl)-pyridine (104 mg) were reacted in the same manner as in Example 4 to obtain the title compound.

Yield: 292 mg (90%).

$^1$H-NMR (400 MHz, CDCl$_3$) δ: 2.91–3.10(m,3H), 3.16 (d,1H,J=13.2 Hz), 3.29–3.44(m,3H), 3.51–3.59(m,1H), 3.86–3.95(m,19H), 4.40(d,1H,J=13.2 Hz), 4.95(d,1H,J=15.4 Hz), 6.98(d,1H,J=4.9 Hz), 7.02(d,1H,J=4.9 Hz), 7.16–7.26 (m,19H), 7.45(s,1H), 7.68(s,1H), 7.72(s,1H), 8.47(d,1H,J=5.1 Hz), 8.51(d,1H,J=4.9 Hz).

EXAMPLE 10

Synthesis of (3S)-3-carbamidomethyl-2-oxo-N,N'-bis[[2-(3,4,5-trimethoxyphenyl)pyridin- 4-yl] methyl]piperazine dihydrochloride

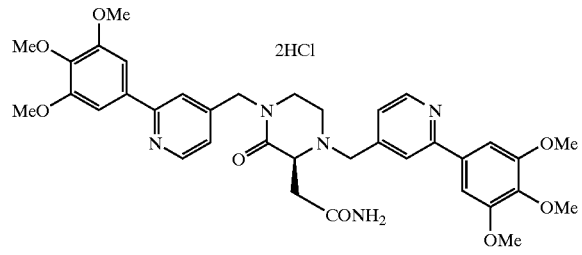

(3S)-2-Oxo-N,N'-bis[[2-(3,4,5-trimethoxyphenyl)-pyridin-4-yl]methyl]-3-[2-(tritylaminocarbonyl)methyl]-piperazine (292 mg) was dissolved in acetic acid (2 mL), and to the solution trifluoroacetic acid (4 m) was added, and the mixture was stirred at 80° C. After completion of the reaction, the reaction mixture was concentrated under reduced pressure, chloroform was added to the residue, and the resultant mixture was washed with a saturated aqueous solution of sodium hydrogencarbonate, water and saturated brine, dried over anhydrous sodium sulfate and concentrated under reduced pressure. The residue was purified by column chromatography on silica gel (chloroform:ammonia-saturated methanol=20:1) to obtain the title compound as a hydrochloride.

Yield: 108 mg (51%).

$^1$H-NMR (400 MHz, CDCl$_3$) δ: 2.64(t,1H,J=10.5 Hz), 2.93–3.00(m,2H), 3.08(d,1H,J=11.7 Hz), 3.37–3.50(m,4H), 3.80(s,3H), 3.82(s,6H), 3.83(s,3H), 3.86(s,6H), 4.02(d,1H, J=15.6 Hz), 4.09(d,1H,J=14.6 Hz), 5.50(d,1H,J=15.4 Hz), 7.05(s,2H), 7.13(s,2H), 7.18(d,1H,J=4.9 Hz), 7.57–7.67(m, 3H), 8.53(d,1H,J=5.1 Hz), 8.82(d,1H,J=5.1 Hz).

m/z (EI) : 671 [M$^+$].

PREPARATION EXAMPLE 52

Synthesis of N-(9-fluorenylmethoxycarbonyl)-L-valyl-N-(benzyl)glycine ethyl ester N-(9-Fluorenylmethoxycarbonyl)-L-valine (1.0 g) was dissolved in a mixed solvent of dichloromethane (10 mL) and DMF (0.1 mL), and to the solution oxalyl chloride (374 mg) was added dropwise at 0° C. The mixture was stirred for 30 minutes and added dropwise into a solution of N-(benzyl) glycine ethyl ester (587 mg) and triethylamine (477 mg) in dichloromethane (10 mL) at 0° C. The resultant mixture was stirred at room temperature for 2 hours, and the reaction mixture was concentrated under reduced pressure. Ethyl acetate was added to the residue, and the mixture was washed with water and saturated brine, dried over anhydrous sodium sulfate and concentrated under reduced pressure. The residue was purified by column chromatography on silica gel (n-hexane:ethyl acetate=3:1) to obtain the title compound.

Yield: 1.37 g (91%).

PREPARATION EXAMPLE 53

Synthesis of cyclo-[N-(benzyl)glycyl-L-valyl]

N-(9-Fluorenylmethoxycarbonyl)-L-valyl-N-(benzyl) glycine ethyl ester (1.23 g) was dissolved in a 20% acetonitrile solution (12 mL) of piperidine, and the solution was stirred at room temperature. After 30 minutes, the reaction mixture was concentrated under reduced pressure. Ethyl acetate was added to the residue, and the mixture was washed with water and saturated brine, dried over anhydrous sodium sulfate and concentrated under reduced pressure. The residue was purified by column chromatography on silica gel (chloroform:methanol=50:1) to obtain the title compound.

Yield: 558 mg (95%).

$^1$H-NMR (400 MHz, CDCl$_3$) δ: 0.88(d,3H,J=6.63 Hz), 1.03(d,3H,J=7.2 Hz), 2.42–2.49(m,1H), 3.77(d,1H,J=17.8 Hz), 3.86(d,1H,J=17.8 Hz), 3.93(t,1H,J=2.9 Hz), 4.45(d,1H, J=14.3 Hz), 4.76(d,1H,J=14.4 Hz), 6.79(br,1H), 7.26–7.37 (m,5H).

PREPARATION EXAMPLE 54

Synthesis of (3S)-1-(benzyl)-3-isopropylpiperazine

Cyclo-[N-(benzyl)glycyl-L-valyl] (558 mg) was dissolved in THF (20 mL), and to the solution lithium aluminum hydride (430 mg) was added at 0° C., and the mixture was stirred at room temperature under an argon atmosphere. After completion of the reaction, a saturated aqueous solution of ammonium chloride was added to the reaction mixture, and an excessive amount of a saturated aqueous solution of sodium hydrogencarbonate was then added to conduct extraction with ethyl acetate. The resultant organic layer was dried over anhydrous sodium sulfate and concentrated under reduced pressure, and the residue was then purified by column chromatography on silica gel (chloroform:methanol=30:1) to obtain the title compound.

Yield: 386 mg (78%).

¹H-NMR (400 MHz, CDCl₃) δ: 0.88(d,3H,J=6.8 Hz), 0.93(d,3H,J=6.8 Hz), 1.51–1.59(m,1H), 1.78(br,2H), 1.98 (dt,1H,J=11.1 Hz,3.1 Hz), 2.46–2.50(m,1H), 2.72(d,1H,J= 10.9 Hz), 2.85–2.89(m,2H), 2.98(dt,1H,J=11.9 Hz,2.7 Hz), 3.44(d,1H,J=13.1Hz), 3.56(d,1H,J=13.1 Hz), 7.23–7.31(m, 5H).

PREPARATION EXAMPLE 55

Synthesis of (2S)-2-isopropylpiperazine (3S)-1-(Benzyl)-3-isopropylpiperazine (358 mg) was dissolved in acetic acid (10 mL), and to the solution 10% palladium on carbon (40 mg) was added, and the mixture was then stirred at 50° C. under a hydrogen atmosphere for 4 hours. The reaction mixture was filtered, and the filtrate was concentrated under reduced pressure. The residue was purified by column chromatography on silica gel (chloroform:ammonia-saturated methanol=20:1) to obtain the title compound.

Yield: 161 mg (77%).

¹H-NMR (400 MHz, CDCl₃) δ: 0.91(d,3H,J=6.8 Hz), 0.93(d,3H,J=6.6 Hz), 1.48–1.57(m,1H), 1.75(br,2H), 2.31–2.45(m,2H), 2.67–2.83(m,2H), 2.90(d,1H,J=11.5 Hz), 2.99–3.02(m,2H).

EXAMPLE 11

Synthesis of (2S)-2-isopropyl-N,N'-bis[[2-(3,4,5-trimethoxyphenyl)pyridin-2-yl]methyl]piperazine trihydrochloride

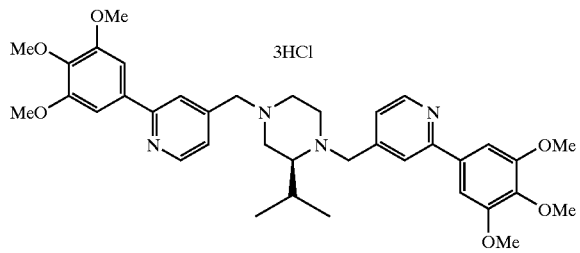

(2S)-2-Isopropylpiperazine (25 mg) and 4-chloromethyl-2-(3,4,5-trimethoxyphenyl)pyridine (117 mg) were reacted in the same manner as in Example 1 to obtain the title compound as a hydrochloride.

Yield: 129 mg (theoretical amount).

¹H-NMR (400 MHz, CDCl₃) δ: 0.95(d,3H,J=6.8 Hz), 0.98(d,3H, J=6.8 Hz), 1.76–1.91(m,1H), 2.14–2.34(m,4H), 2.62(d,1H,J=10.1 Hz), 2.76–2.82(m,2H), 3.24(d,1H,J=14.4 Hz), 3.50(d,1H,J=14.1 Hz), 3.62(d,1H,J=14.1 Hz), 3.90(s, 6H), 3.96(s,6H), 3.97(s,6H), 4.17(d,1H,J=14.4 Hz), 7.21–7.27(m,6H), 7.64(s,1H), 7.65(s,1H), 8.58(d,1H,J=4.7 Hz), 8.59(d,1H,4.5 Hz).

m/z (EI): 642 [M⁺].

PREPARATION EXAMPLE 56

Synthesis of N-(9-fluorenylmethoxycarbonyl)-L-leucyl-N-(benzyl)glycine ethyl ester N-(9-Fluorenylmethoxycarbonyl)-L-leucine (1.31 g) and N-(benzyl)glycine ethyl ester (738 mg) were reacted in the same manner as in Preparation Example 52 to obtain the title compound.

Yield: 1.65 g (84%).

PREPARATION EXAMPLE 57

Synthesis of cyclo-[N-(benzyl)glycyl-L-leucyl]

N-(9-Fluorenylmethoxycarbonyl)-L-leucyl-N-(benzyl) glycine ethyl ester (1.79 g) was reacted in the same manner as in Preparation Example 53 to obtain the title compound.

Yield: 775 mg (88%).

¹H-NMR (400 MHz, CDCl₃) δ: 0.95(d,3H,J=6.5 Hz), 0.98(d,3H,J=6.5 Hz), 1.62–1.67(m,1H), 1.75–1.85(m,2H), 3.80(d,1H,J=17.4 Hz), 3.86(d,1H,J=17.2 Hz), ₈04.04(dt,1H, J=6.1 Hz,3.2 Hz), 4.54(d,1H,J=14.3 Hz), 4.65(d,1H,J=14.4 Hz), 6.80(br,1H), 7. 24–7.37(m, 5H)

PREPARATION EXAMPLE 58

Synthesis of (3S)-1-(benzyl)-3-(2-methylpropyl) piperazine

Cyclo-[N-(benzyl)glycyl-L-leucyl] (775 mg) was treated in the same manner as in Preparation Example 54 to obtain the title compound.

Yield: 700 mg (theoretical amount).

¹H-NMR (400MHz, CDCl₃) δ: 0.87(d,3H,J=6.4 Hz), 0.89 (d,3H,J=6.6 Hz), 1.08–1.26(m,2H), 1.61–1.71(m,3H), 2.00 (dt,1H,J=11.1 Hz,3.6 Hz), 2.73–2.96(m,5H), 3.39–3.58(m, 2H), 7.23–7.31(m,5H).

PREPARATION EXAMPLE 59

Synthesis of (2S)-2-(2-methylpropyl)piperazine (3S)-1-(Benzyl)-3-(2-methylpropyl)piperazine (700 mg) was treated in the same manner as in Preparation Example 55 to obtain the title compound.

Yield: 308 mg (72%).

¹H-NMR (400 MHz, CDCl₃) δ: 0.89(d,3H,J=6.6 Hz), 0.91(d,3H,J=6.6 Hz), 1.10–1.23(m,2H), 1.56(br,2H), 1.60–1.69(m,1H), 2.34(dd,1H,J=11.8 Hz,9.9 Hz), 2.64–2.98 (m,6H).

EXAMPLE 12

Synthesis of (2S)-2-(2-methylpropyl)-N,N'-bis[[2-(3,4,5-trimethoxyphenyl)pyridin-2-yl]methyl] piperazine trihydrochloride

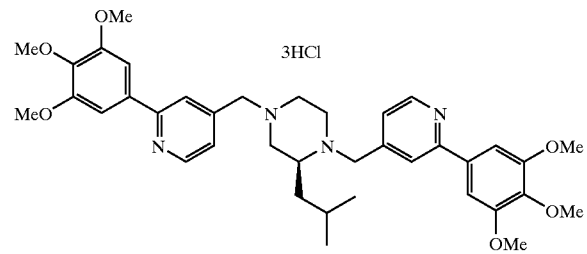

(2S)-2-(2-Methylpropyl)piperazine (28 mg) and 4-chloromethyl-2-(3,4,5-trimethoxyphenyl)pyridine (117 mg) were reacted in the same manner as in Example 1 to obtain the title compound as a hydrochloride.

Yield: 129 mg (99%).

¹H-NMR (400 MHz, CDCl₃) δ: 0.86(d,3H,J=6.1 Hz) 0.90(d,3H,J=6.1 Hz), 1.50–1.56(m,3H), 2.25–2.78(m,7H), 3.39(d,1H,J=14.1 Hz), 3.51(d,1H,J=14.1 Hz), 3.62(d,1H,J=14.1 Hz), 3.90(s,6H), 3.97(br,13H), 7.22–7.27(m,6H), 7.65(s,2H), 8.59(d,1H,J=5.3 Hz), 8.60(d,1H,J=5.5 Hz).

m/z (EI): 656 [M⁺].

PREPARATION EXAMPLE 60

Synthesis of N-(9-fluorenylmethoxycarbonyl)-L-isoleucyl-N-(benzyl)glycine ethyl ester N-(9-Fluorenylmethoxycarbonyl)-L-isoleucine (1.36 g) and N-(benzyl)glycine ethyl ester (770 mg) were reacted in the same manner as in Preparation Example 52 to obtain the title compound.

Yield: 1.73 g (85%).

PREPARATION EXAMPLE 61

Synthesis of cyclo-[N-(benzyl)glycyl-L-isoleucyl]

N-(9-Fluorenylmethoxycarbonyl)-L-isoleucyl-N-(benzyl)glycine ethyl ester (1.63 g) was reacted in the same manner as in Preparation Example 53 to obtain the title compound.

Yield: 973 mg (including impurities).

¹H-NMR (400 MHz, CDCl₃) δ: 0.90 (t,3H,J=7.4 Hz), 1.00(d,3H,J=7.2 Hz), 1.14–1.25(m,1H), 1.35–1.43(m,1H), 2.09–2.15(m,1H), 3.77(d,1H,J=18.0 Hz), 3.85(d,1H,J=17.8 Hz), 3.95–3.97(m,1H), 4.51(d,1H,J=14.3 Hz), 4.69(d,1H,J=14.4 Hz), 7.25–7.36(m,6H).

PREPARATION EXAMPLE 62

Synthesis of (3S)-1-(benzyl)-3-(1-methylpropyl)piperazine

Cyclo-[N-(benzyl)glycyl-L-isoleucyl] (973 mg, including impurities) was treated in the same manner as in Preparation Example 54 to obtain the title compound.

Yield: 506 mg (71% by 2 steps).

¹H-NMR (400 MHz, CDCl₃) δ: 0.87(d,3H,J=6.8 Hz), 0.87(t,3H,J=7.4 Hz), 1.13–1.20(m,1H), 1.30–1.41(m,1H), 1.46–1.70(m,2H), 1.78(t,1H,J=10.4 Hz), 1.97(dd,1H,J=11.1 Hz,3.3 Hz), 2.57–2.62(m,1H), 2.68–2.76(m,1H), 2.82–2.89(m,2H), 2.97(dt,1H,J=11.9 Hz,2.7 Hz), 3.44(d,1H,J=13.1 Hz), 3.56(d,1H,J=13.1 Hz), 7.24–7.31(5H).

PREPARATION EXAMPLE 63

Synthesis of (2S)-2-(1-methylpropyl)piperazine (3S)-1-(Benzyl)-3-(1-methylpropyl)piperazine (506 mg) was treated in the same manner as in Preparation Example 55 to obtain the title compound.

Yield: 202 mg (65%).

¹H-NMR (400 MHz, CDCl₃) δ: 0.87 (d,3H,J=6.8 Hz), 0.89(t,3H, J=7.4 Hz), 1.12–1.23(m,1H), 1.29–1.32(m,1H), 1.44–1.52(m,1H), 1.64(br,2H), 2.40–2.48(m,2H), 2.69(dt, 1H,J=11.3 Hz,2.9 Hz), 2.80(dt,1H,J=11.3 Hz,2.7 Hz), 2.89 (d,1H,J=11.5 Hz), 2.94–3.01(m,2H).

EXAMPLE 13

Synthesis of (2S)-2-(1-methylpropyl)-N,N'-bis[[2-(3,4,5-trimethoxyphenyl)pyridin-2-yl]methyl]piperazine trihydrochloride

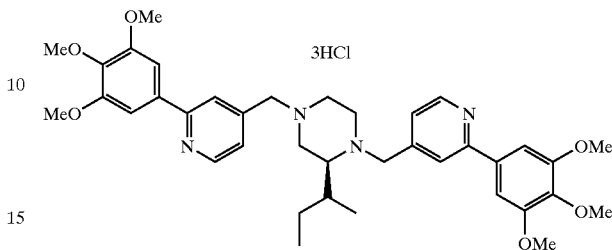

(2S)-2-(1-Methylpropyl)piperazine (28 mg) and 4-chloromethyl-2-(3,4,5-trimethoxyphenyl)pyridine (117 mg) were reacted in the same manner as in Example 1 to obtain the title compound as a hydrochloride.

Yield: 117 mg (90%).

¹H-NMR (400 MHz, CDCl₃) δ: 0.93 (t,3H,J=7.8 Hz), 0.95(d,3H,J=6.6 Hz), 1.16–1.25(m,1H), 1.35–1.41(m,1H), 1.90–2.05(m,1H), 2.11–2.32(m,3H), 2.45(br,1H), 2.65(d, 1H,J=10.3 Hz), 2.74–2.79(m,2H), 3.17(d,1H,J=14.3 Hz), 3.52(d,1H,J=14.1 Hz), 3.60(d,1H,J=14.1 Hz), 3.90(s,6H), 3.96(s,6H), 3.97(s,6H), 4.19(d,1H,J=14.2 Hz), 7.21–7.27(m, 6H), 7.65(s,2H), 8.58(d,1H,J=3.1 Hz), 8.60(d,1H,J=3.1 Hz).

m/z (EI): 656 [M⁺]

Test Example 1

(Inhibitory Effect on Cell Adhesion)

This test was conducted by reference to the method of Ross et al. (J. Biol. Chem., 267, 8537–8543 (1992)). More specifically, after human umbilical venous endothelial cells (HUVEC) were cultured on a 48-well plate to confluent growth, TNFα was added thereto. Upon elapsed time of 5 hours after the addition, U937, which is a human monocytic/histocytic cell fluorescence-labeled with PKH2 (product of Dainippon Pharmaceutical Co., Ltd.), was added in a proportion of 1×10⁶ cells per well. After the plate was left at rest at room temperature for 1 hour, unadhered U937 was washed out and lysed in 1% Triton X-100 to measure a remaining fluorescence intensity (excitation wavelength: 480 nm; measuring wavelength: 530 nm). HUVEC and U937 were cultured in EGM-2 (product of Sanko Junyaku K.K.) and 10% FCS-containing RPMI1640, respectively. Each test agent was added to HUVEC upon the addition of TNFα and to U937 24 hours prior to the cell adhesion test. The inhibitory activity was calculated out according to the equation [100–(C–B)/(A–B)×100 (%)], wherein A is the number of U937 cells adhered to HUVEC stimulated by TNFα when no test agent was added, B is the number of U937 cells adhered to HUVEC not stimulated by TNFα when no test agent was added, and C is the number of U937 cells adhered to HUVEC stimulated by TNFα when the test agent was added. The results are shown in Table 1. As control compounds, Test Compound 1 described in Japanese Patent Application Laid-Open No. 9-143075 and dilazep described in Japanese Patent Application Laid-Open No. 11-92382 were simultaneously evaluated.

TABLE 1

Inhibitory activity of each compound at 1, 10 μM against cell adhesion

| Example | Percent inhibition (%) | |
|---|---|---|
| | 1 μM | 10 μM |
| 1 | 76 | 78 |
| 2 | 42 | 64 |
| 3 | 34 | 90 |
| 4 | 60 | 79 |
| 5 | 51 | 85 |
| 6 | 63 | 77 |
| 7 | 51 | 70 |
| 8 | 63 | 79 |
| 9 | 38 | 86 |
| Test compound 1 | 5 | 51 |
| Dilazep | 12 | 25 |

Specific formulation examples will hereinafter be described.

PREPARATION EXAMPLE 64

Capsule Preparation

| | |
|---|---|
| (3S)-3-Isopropyl-2-oxo-N,N'-bis[[2-(3,4,5-trimethoxyphenyl)pyridin-4-yl]methyl]-piperazine sesquihydrochloride | 30 mg |
| Microcrystalline cellulose | 30 mg |
| Lactose | 30 mg |
| Magnesium stearate | 3 mg |
| Total amount | 93 mg. |

The above ingredients were mixed in accordance with a method known per se in the art and then charged in a gelatin capsule to obtain a capsule preparation.

PREPARATION EXAMPLE 65

Table Preparation

| | |
|---|---|
| (3S)-3-Isopropyl-2-oxo-N,N'-bis[[2-(3,4,5-trimethoxyphenyl)pyridin-4-yl]methyl]-piperazine sesquihydrochloride | 30 mg |
| Starch | 44 mg |
| Starch (for glue) | 5.6 mg |
| Magnesium stearate | 0.4 mg |
| Calcium carboxymethyl cellulose | 20 mg |
| Total amount | 100 mg. |

The above ingredients were mixed in accordance with a method known per se in the art to obtain a tablet preparation.

PREPARATION EXAMPLE 66

Injection Preparation (3S)-3-Isopropyl-2-oxo-N,N'-bis[[2-(3,4,5-trimethoxyphenyl)pyridin-4-yl]methyl]piperazine sesquihydrochloride (100 mg) and sodium chloride (900 mg) were dissolved in distilled water (about 80 mL) for injection, and distilled water for injection was added to the resultant solution to 100 mL in total. This diluted solution was sterilized by filtration and then subdivided and charged into 10 light-screening ampoules, and the ampoules were sealed to obtain sterile injection preparations.

As described above, the compounds (1) according to the present invention have excellent inhibitory effects on both cell adhesion and cell infiltration and are useful for prevention or treatment of diseases such as allergy, asthma, rheumatism, arteriosclerosis and inflammation.

Obviously, numerous modifications of the above teachings are apparent to those skilled in the art. Therefore, within the scope of the appended claims the invention can be practiced otherwise than as specifically described herein.

What is claimed is:

1. A piperazine compound of formula (1):

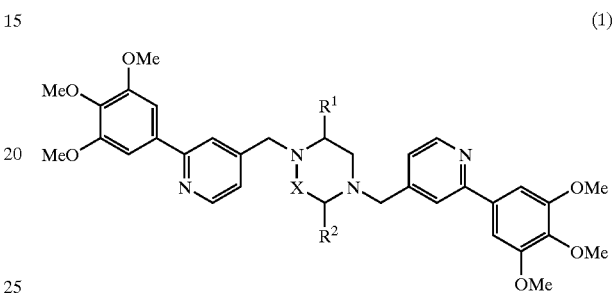

(1)

wherein X is —$CH_2$—, —C(O)— or —CH($CH_3$)—; $R^1$ is a hydrogen atom or alkyl group; and $R^2$ is a hydrogen atom, alkyl group, hydroxyalkyl group, arylalkyl group, heteroarylalkyl group, carboxyalkyl group, carboxamidoalkyl group, aminoalkyl group or guanidinoalkyl group;

an acid-addition salt thereof, or a hydrate thereof.

2. The piperazine compound of claim 1, wherein $R^1$ is a hydrogen atom or $C_1$–$C_6$-alkyl group; and $R^2$ is a hydrogen atom, $C_1$–$C_6$-alkyl group, hydroxy-$C_1$–$C_6$-alkyl group, $C_6$–$C_{10}$-aryl-$C_1$–$C_6$-alkyl group, 5- or 6-membered heteroaryl-$C_1$–$C_6$-alkyl group having 1 or 2 nitrogen atoms, carboxy-$C_1$–$C_6$-alkyl group, carboxamido-$C_1$–$C_6$-alkyl group, amino-$C_1$–$C_6$-alkyl group or guanidino-$C_1$–$C_6$-alkyl group.

3. A pharmaceutical composition comprising as an active ingredient, a piperazine compound of formula (1):

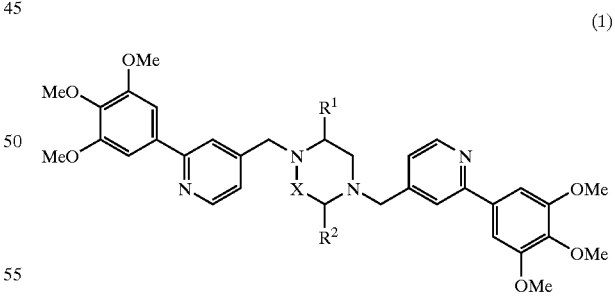

(1)

wherein X is —$CH_2$—, —C(O)— or —CH($CH_3$)—; $R^1$ is a hydrogen atom or alkyl group; and $R^2$ is a hydrogen atom, alkyl group, hydroxyalkyl group, arylalkyl group, heteroarylalkyl group, carboxyalkyl group, carboxamidoalkyl group, aminoalkyl group or guanidinoalkyl group;

an acid-addition salt thereof, or a hydrate thereof, and a pharmaceutically acceptable carrier.

4. The composition of claim 3, wherein $R^1$ is a hydrogen atom or $C_1$–$C_6$-alkyl group; and $R^2$ is a hydrogen atom, $C_1$–$C_6$-alkyl group, hydroxy-$C_1$–$C_6$-alkyl group, $C_6$–$C_{10}$-aryl-$C_1$–$C_6$-alkyl group, 5- or 6-membered heteroaryl-$C_1$–$C_6$-alkyl group having 1 or 2 nitrogen atoms, carboxy-$C_1$–$C_6$-alkyl group, carboxamido-$C_1$–$C_6$-alkyl group, amino-$C_1$–$C_6$-alkyl group or guanidino-$C_1$–$C_6$-alkyl group.

5. The composition of claim 3, comprising an effective amount of the piperazine compound for treating a disease caused by cell adhesion and/or cell infiltration.

6. The composition of claim 5, wherein the disease is selected from the group consisting of allergy, asthma, inflammation, rheumatism and arteriosclerosis.

7. A method for treating a disease selected from the group consisting of allergy, asthma, inflammation, rheumatism, autoimmune disease and arteriosclerosis, which comprises administering to a patient in need thereof a piperazine compound of formula (1)

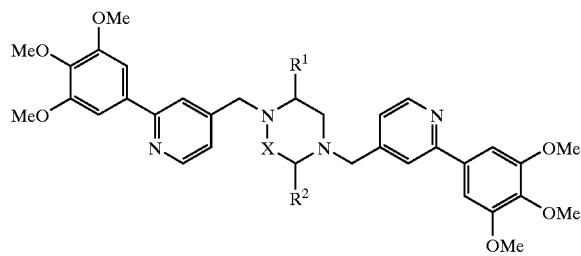

wherein X is —$CH_2$—, —C(O)— or —CH($CH_3$)—; $R^1$ is a hydrogen atom or alkyl group, and $R^2$ is a hydrogen atom, alkyl group, hydroxyalkyl group, arylalkyl group, heteroarylalkyl group, carboxyalkyl group, carboxamidoalkyl group, aminoalkyl group or guanidinoalkyl group;

an acid-addition salt thereof, or a hydrate thereof.

8. The method of claim 7, wherein $R^1$ is a hydrogen atom or $C_1$–$C_6$-alkyl group; and $R^2$ is a hydrogen atom, $C_1$–$C_6$-alkyl group, hydroxy-$C_1$–$C_6$-alkyl group, $C_6$–$C_{10}$-aryl-$C_1$–$C_6$-alkyl group, 5- or 6-membered heteroaryl-$C_1$–$C_6$-alkyl group having 1 or 2 nitrogen atoms, carboxy-$C_1$–$C_6$-alkyl group, carboxamido-$C_1$–$C_6$-alkyl group, amino-$C_1$–$C_6$-alkyl group or guanidino-$C_1$–$C_6$-alkyl group.

9. The method of claim 7, wherein said disease is asthma and wherein said disease comprises infiltration of eosinophils into a bronchus.

10. The method of claim 7, wherein said disease is arteriosclerosis and wherein said disease comprises infiltration of macrophages and T lymphocytes into the aorta.

11. The method of claim 7, wherein said disease is inflammation and wherein said disease comprises infiltration of T lymphocytes and eosinophils into the skin.

12. The method of claim 7, wherein said disease is rheumatism and wherein said disease comprises infiltration of leukocytes into rheumatoid synovial tissue.

13. The method of claim 7, wherein said disease is allergy, said allergy disease selected from the group consisting of bronchial asthma, dermatitis, rhinitis and conjunctivitis.

14. The method of claim 7, wherein said disease is an autoimmune disease selected from the group consisting of rheumatoid arthritis, nephritis, inflammatory bowel disease, diabetes, and chronic inflammatory disease.

15. The method of claim 7, wherein said disease is inflammation of the colon.

16. The method of claim 7, wherein said piperazine compound is administered in a dose of from 1 to 1,0000 mg per day.

17. The method of claim 7, wherein said piperazine compound is administered orally.

18. The method of claim 7, wherein said piperazine compound is administered parenterally.

19. The method of claim 7, wherein said piperazine compound is selected from the group consisting of (3S)-3-Isopropyl-2-oxo-N,N'-bis[[2-(3,4,5-trimethoxyphenyl)pyridin-4-yl]methyl]-piperazine sesquihydrochloride, cis-N,N'-bis[[2-(3,4,5-trimethoxyphenyl)pyridin-4-yl]methyl]-2,6-dimethylpiperazine tetrahydrochloride, trans-N,N'-bis[[2-(3,4,5-trimethoxyphenyl)-pyridin-4-yl]methyl]-2,5-dimethylpiperazine tetrahydrochloride, N,N'-bis[[2-(3,4,5-trimethoxyphenyl)pyridin-4-yl]methyl]-2-hydroxymethylpiperazine dimaleate, 2-oxo-N,N'-bis[[2-(3,4,5-trimethoxyphenyl)-pyridin-4-yl]methyl]piperazine 2.5 hydrochloride, (3S)-3-methyl-2-oxo-N,N'-bis[[2-(3,4,5-trimethoxyphenyl)pyridin-4-yl]methyl]piperazine 2.5 hydrochloride, (3R)-3-isopropyl-2-oxo-N,N'-bis[[2-(3,4,5-trimethoxyphenyl)pyridin-4-yl]methyl]piperazine trihydrochloride, (3S)-3-(2-methylpropyl)-2-oxo-N,N'-bis[[2-(3,4,5-trimethoxyphenyl)pyridin-4 -yl]methyl]piperazine 2.5 hydrochloride, and (3S)-3-benzyl-2-oxo-N,N'-bis[[2-(3,4,5-trimethoxyphenyl)pyridin-4-yl]methyl]piperazine sesquihydrochloride.

20. The piperazine compound of claim 1, which is selected from the group consisting of (3S)-3-Isopropyl-2-oxo-N,N'-bis[[2-(3,4,5-trimethoxyphenyl)pyridin-4-yl]methyl]-piperazine sesquihydrochloride, cis-N,N'-bis[[2-(3,4,5-trimethoxyphenyl)pyridin-4-yl]methyl]-2,6-dimethylpiperazine tetrahydrochloride, trans-N,N'-bis[[2-(3,4,5-trimethoxyphenyl)-pyridin-4-yl]methyl]-2,5-dimethylpiperazine tetrahydrochloride, N,N'-bis[[2-(3,4,5-trimethoxyphenyl)pyridin-4-yl]methyl]-2-hydroxymethylpiperazine dimaleate, 2-oxo-N,N'-bis[[2-(3,4,5-trimethoxyphenyl)-pyridin-4-yl]methyl]piperazine 2.5 hydrochloride, (3S)-3-methyl-2-oxo-N,N'-bis[[2-(3,4,5-trimethoxyphenyl)pyridin-4-yl]methyl]piperazine 2.5 hydrochloride, (3R)-3-isopropyl-2-oxo-N,N'-bis[[2-(3,4,5-trimethoxyphenyl)pyridin-4-yl]methyl]piperazine trihydrochloride, (3S)-3-(2-methylpropyl)-2-oxo-N,N'-bis[[2-(3,4,5-trimethoxyphenyl)pyridin-4-yl]methyl]piperazine 2.5 hydrochloride, and (3S)-3-benzyl-2-oxo-N,N'-bis[[2-(3,4,5-trimethoxyphenyl)pyridin-4-yl]methyl]piperazine sesqui-hydrochloride.

21. The composition of claim 3, wherein said piperazine compound is selected from the group consisting of (3S)-3-Isopropyl-2-oxo-N,N'-bis[[2-(3,4,5-trimethoxyphenyl)pyridin-4-yl]methyl]-piperazine sesquihydrochloride, cis-N,N'-bis[[2-(3,4,5-trimethoxyphenyl)pyridin-4-yl]methyl]-2,6-dimethylpiperazine tetrahydrochloride, trans-N,N'-bis[[2-(3,4,5-trimethoxyphenyl)-pyridin-4-yl]methyl]-2,5-dimethylpiperazine tetrahydrochloride, N,N'-bis[[2-(3,4,5-trimethoxyphenyl)pyridin-4-yl]methyl]-2-hydroxymethylpiperazine dimaleate, 2-oxo-N,N'-bis[[2-(3,4,5-trimethoxyphenyl)-pyridin-4-yl]methyl]piperazine 2.5 hydrochloride, (3S)-3-methyl-2-oxo-N,N'-bis[[2-(3,4,5-trimethoxyphenyl)pyridin-4-yl]methyl]piperazine 2.5 hydrochloride, (3R)-3-isopropyl-2 -oxo-N,N'-bis[[2-(3 ,4,5-trimethoxyphenyl)pyridin-4-yl]methyl]piperazine trihydrochloride, (3S)-3 -(2-methylpropyl)-2-oxo-N,N'-bis[[2-(3 ,4,5-trimethoxyphenyl)pyridin-4-yl]methyl]piperazine 2.5 hydrochloride, and (3S)-3-benzyl-2-oxo-N,N'-bis[[2-(3,4,5-trimethoxyphenyl]pyridin-4-yl]methyl]piperazine sesqui-hydrochloride.

* * * * *

UNITED STATES PATENT AND TRADEMARK OFFICE
CERTIFICATE OF CORRECTION

PATENT NO.    : 6,432,957 B1                                                                Page 1 of 1
DATED         : August 13, 2002
INVENTOR(S)   : Kodama et al.

It is certified that error appears in the above-identified patent and that said Letters Patent is hereby corrected as shown below:

<u>Title page,</u>
Items [12] and [75], the first inventor's name should read:
-- [12] United States Patent
         Kodama et al. --
-- [75] Inventors:  Tatsuhiko Kodama, Tokyo; Masahiro Tamura, Higashimurayama; Toshiaki Oda, Higashimurayama; Yukiyoshi Yamazaki, Higashimurayama; Masahiro Nishikawa, Higashimurayama; Takeshi Doi, Higashimurayama; Yoshinori Kyotani, Higashimurayama; all of (JP) --

Signed and Sealed this

Thirty-first Day of December, 2002

JAMES E. ROGAN
*Director of the United States Patent and Trademark Office*